US012778548B2

(12) United States Patent
Sokulin et al.

(10) Patent No.: US 12,778,548 B2
(45) Date of Patent: Nov. 3, 2026

(54) SYSTEMS FOR AUTOMATED BI-PLANE ULTRASOUND IMAGING

(71) Applicant: GE Precision Healthcare LLC, Waukesha, WI (US)

(72) Inventors: Ella Sokulin, Kiryat Tivon (IL); Carmit Shiran, Kiryat Tivon (IL); Alexander Sokulin, Kiryat Tivon (IL); Doron Shaked, Kiryat Tivon (IL)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/943,721

(22) Filed: Nov. 11, 2024

(65) Prior Publication Data

US 2026/0130643 A1 May 14, 2026

(51) Int. Cl.
*A61B 8/00* (2006.01)
*A61B 8/08* (2006.01)

(52) U.S. Cl.
CPC .......... *A61B 8/4444* (2013.01); *A61B 8/0875* (2013.01); *A61B 8/461* (2013.01); *A61B 8/5223* (2013.01)

(58) Field of Classification Search
CPC ......... A61B 8/08; A61B 8/0875; A61B 8/461; A61B 8/5223
See application file for complete search history.

(56) References Cited

U.S. PATENT DOCUMENTS 11,264,135 B2 3/2022 Rao et al.
11,517,290 B2 12/2022 Aase et al.
2006/0034513 A1 2/2006 Cai
2008/0304729 A1 12/2008 Peszynski
2017/0007207 A1* 1/2017 Gauthier ................ A61B 8/145
2019/0105013 A1* 4/2019 Wang ...................... A61B 8/463
2019/0328361 A1* 10/2019 Halmann .............. G06T 3/4038
2020/0289096 A1* 9/2020 Aase ...................... A61B 8/469
2021/0350539 A1 11/2021 Halmann

FOREIGN PATENT DOCUMENTS

JP 6180539 B2 8/2017

OTHER PUBLICATIONS

EP application 25209376.0 filed Oct. 17, 2025—extended Search Report issued Mar. 5, 2026; 8 pages.

* cited by examiner

*Primary Examiner* — Chao Sheng
(74) *Attorney, Agent, or Firm* — Foley & Lardner LLP

(57) ABSTRACT

Systems are provided for automating bi-plane ultrasound imaging. In one example, an ultrasound imaging system includes a processing circuit having a processor coupled to a memory device storing instructions thereon that, when executed, cause the processing circuit to perform operations. The operations include receiving a first image dataset obtained by an ultrasound probe along two or more planes of a first orientation in a field of view; identifying at least one secondary anatomical feature based on the first image dataset; determining an additional plane oriented according to the at least one secondary anatomical feature in the field of view; automatically aligning a scanning plane of the ultrasound probe with the additional plane; receiving second image data obtained by the ultrasound probe along the additional plane; and displaying a bi-plane image, the bi-plane image based on an image from the first image dataset and the second image data.

20 Claims, 13 Drawing Sheets

900a

900b

SYSTEMS FOR AUTOMATED BI-PLANE ULTRASOUND IMAGING

STATEMENT REGARDING FEDERALLY SPONSORED RESEARCH AND DEVELOPMENT

This invention was made with government support under Grant No. 75A50123C00035 awarded by Biomedical Advanced Research and Development Authority (BARDA). The Government has certain rights in the invention.

FIELD

Embodiments of the subject matter disclosed herein relate to ultrasound imaging, and more particularly, to automating bi-plane navigation of a probe during a lung ultrasound scan.

BACKGROUND

During an ultrasound scan of a lung, an ultrasound probe is placed in a first orientation (e.g., a sagittal orientation towards a patient's head) by a technician, such as a sonographer. When a pathology is detected during the ultrasound scan, however, the technician may move the ultrasound probe from the first orientation to a second orientation (e.g., a transverse orientation). The ultrasound scan continues by collecting ultrasound data using the ultrasound probe in the second orientation. The images obtained during the ultrasound scan of the lung depict anatomical features such as rib bones, shadows of the rib bones, a pleura (e.g., tissue covering the lungs), and so on.

SUMMARY

An embodiment relates to an ultrasound imaging system. The ultrasound imaging system includes a processing circuit. The processing circuit includes a processor coupled to a memory device, and the memory device stores instructions thereon that, when executed, cause the processing circuit to perform operations including receiving a first image dataset obtained by an ultrasound probe along two or more planes of a first orientation in a field of view, identifying at least one secondary anatomical feature based on the first image dataset, determining an additional plane oriented according to the at least one secondary anatomical feature in the field of view, automatically aligning a scanning plane of the ultrasound probe with the additional plane, receiving second image data obtained by the ultrasound probe along the additional plane, and displaying a bi-plane image on a display device of the ultrasound imaging system, the bi-plane image based on an image from the first image dataset and the second image data.

Another embodiment relates to an ultrasound imaging system. The ultrasound imaging system includes an image processing circuit configured to identify at least one secondary anatomical feature based on the first image dataset obtained by an ultrasound probe along two or more planes of a first orientation in a field of view, wherein an additional plane is oriented according to the at least one secondary anatomical feature in the field of view, and wherein second image data is obtained by the ultrasound probe along the additional plane. The ultrasound imaging system includes a control circuit configured to automatically align a scanning plane of the ultrasound probe with the additional plane. The ultrasound imaging system includes a display device configured to display a bi-plane image based on an image from the first image dataset and the second image data.

Another embodiment relates to a method. The method includes receiving, by a processing circuit of an ultrasound imaging system, a first image dataset obtained by an ultrasound probe along two or more planes of a first orientation in a field of view. The method includes identifying, by the processing circuit, at least one secondary anatomical feature based on the first image dataset. The method includes determining, by the processing circuit, an additional plane oriented according to the at least one secondary anatomical feature in the field of view. The method includes automatically aligning, by the processing circuit, a scanning plane of the ultrasound probe with the additional plane. The method includes receiving, by the processing circuit, second image data obtained by the ultrasound probe along the additional plane. The method includes displaying, by the processing circuit, a bi-plane image on a display device of the ultrasound imaging system.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
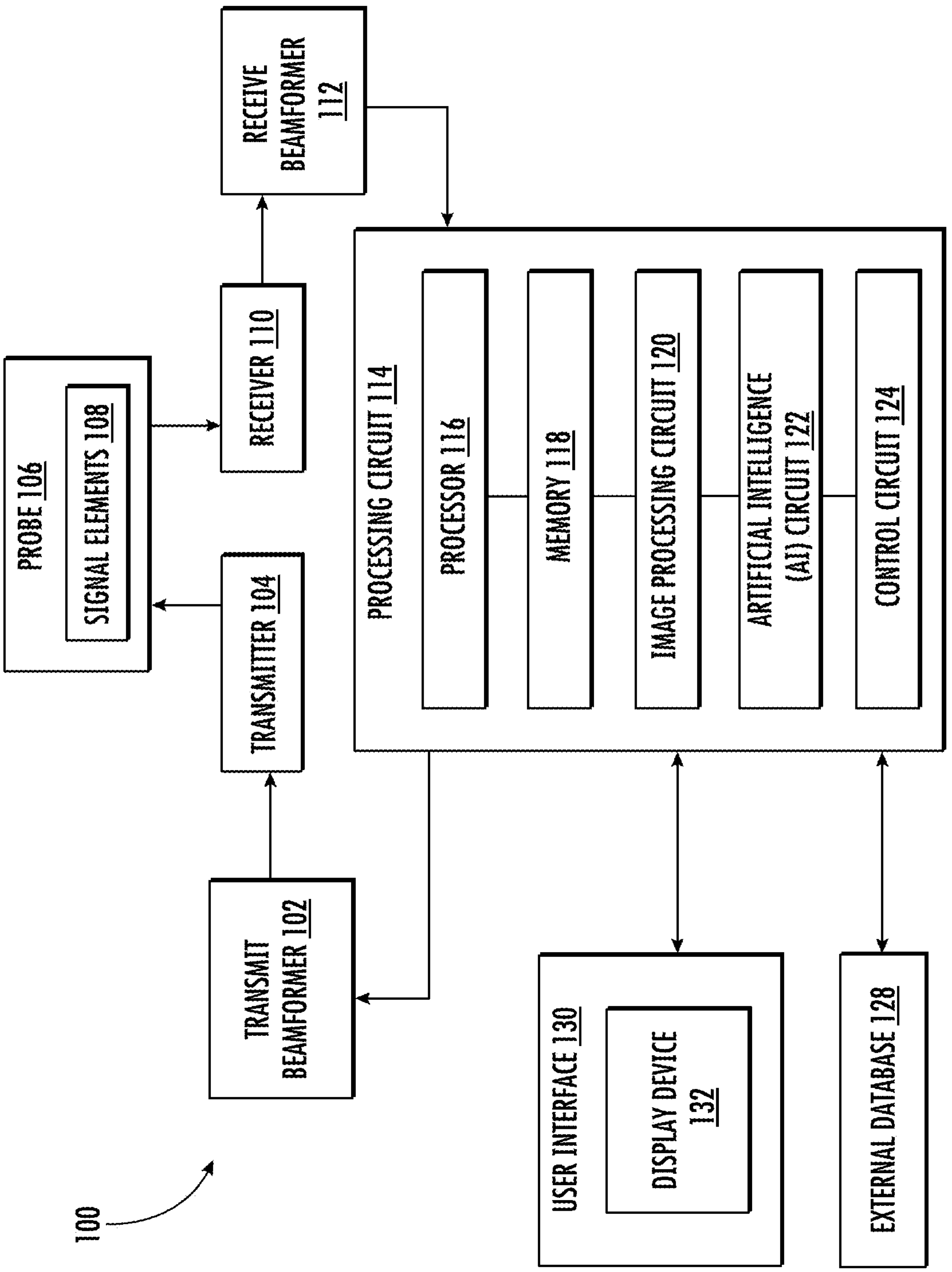
FIG. 1 is a block diagram of an ultrasound imaging system, according to an example embodiment.

Referring generally to the figures, systems and methods for automating bi-plane steering during an ultrasound scan are disclosed. The systems disclosed herein are used to automatically orient a second scanning plane (e.g., in addition to a sagittal view) to match an orientation of the ribs and/or a detected pathology during a lung ultrasound. Therefore, the second scanning plane is determined based on a detection of the orientation of the ribs, as described herein. The systems and methods use a matrix probe configured to collect ultrasound data from any direction, such that the matrix probe is configured to automatically align a scanning plane with the determined second scanning plane.

During an ultrasound scan, an ultrasound probe is conventionally positioned in a sagittal orientation (e.g., pointed towards a patient's head). With this view, however, the curvature of the ribs causes the lung to be obstructed in the ultrasound images by one or more rib bones. That is, it is desired to orient the probe such that the scanning plane aligns between two rib bones, and therefore the image of the lung is unobstructed. Therefore, orienting the ultrasound probe such that the scanning plane aligns with the curvature of the rib bones is time consuming and relies on the skills/expertise of the operator (e.g., sonographer, technician, clinician, etc.). The curvature of the ribs varies between patients, meaning the operator's skills/expertise relating to probe navigation also rely on the specific anatomy of the patient being imaged, which the operator typically lacks.

Furthermore, when a pathology is detected from the image data, positioning the probe such that the scanning plane aligns with the curvature of the ribs and intersects the pathology requires additional precision, skill, and expertise of the operator. That is, when a pathology is detected, operators switch the scanning plane from a sagittal view to a transverse view in order to estimate an orthogonal extent of the pathology. Therefore, a bi-plane image (e.g., including the sagittal view and the transverse view) is used to generate comprehensive ultrasound images, particularly in the case of a detected pathology. Because of the curvature of the rib bones, however, the optimal transverse view (e.g., with minimal obstruction from the rib bones), is not a scanning plane that is perpendicular to the sagittal plane.

The systems and methods described herein provide a technical solution to existing ultrasound imaging systems by implementing a three-dimensional probe configured to capture ultrasound data from any direction/plane and adjusting a scanning plane of the probe based on an assessment of a patient's anatomy. Therefore, the second scanning plane (e.g., the transverse plane) may be automatically aligned with the curvature of the ribs, as described herein, such that the rib bones cause minimal obstruction to the ultrasound image and such that the operator does not have to manually maneuver the probe to an optimal position for obtaining image data from the second scanning plane. Furthermore, using the systems and methods described herein, the bi-plane image can be centered around a location of a pathology.

Thus, the systems and methods described herein reduce the dependency on the expertise and skills of the operator by automatically steering the probe to a scanning plane between the ribs, thereby reducing the need for the operator to maneuver the probe manually to reach that view. Furthermore, the systems and methods described herein assist an operator in detecting a pathology and/or completing an ultrasound exam in a shorter amount of time (e.g., due to the operator not having to manually adjust the probe in order to obtain the desired scanning planes).

The implementations described herein address a technical problem by providing enhanced data integration and analysis capabilities, which deliver a particular technical solution that streamlines and refines generating bi-plane images during a lung ultrasound. The systems described herein are implemented to improve how data is synthesized and utilized from various sources that provide information relating to an optimal adjustment of a probe for capturing images during an ultrasound scan. By assessing specific anatomical features and automatically adjusting a scanning plane of the probe based on the assessment, these systems provide real-time guidance for generating bi-plane images during an ultrasound scan. Accordingly, this approach provides a specific technical improvement to various technical problems, including those set forth herein. The systems described herein may also reduce processing power by performing various processing operations simultaneously to generate bi-plane images during an ultrasound scan, rather than performing a plurality of processing operations individually and consuming unnecessary processing power.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring to FIG. 1, a schematic diagram of an ultrasound imaging system 100 is shown. The ultrasound imaging system 100 may be used in a medical environment (e.g., hospitals, clinics, etc.), for example, by a sonographer, technician, or other clinician certified to collect ultrasound data from a patient.

An example of a procedure performed using the ultrasound imaging system 100 may be a lung ultrasound. The lung ultrasound may be performed to detect various pulmonary pathologies such as pneumonia, pulmonary edema, pleural effusion, pneumothorax (e.g., a collapsed lung), pulmonary embolism, lung cancer, and so on. Such pathologies are detected by collecting and processing ultrasound data (e.g., using the ultrasound imaging system 100, as described herein). During the lung ultrasound, a sonographer collects the ultrasound data by navigating a probe (e.g., probe 106, as described below) over a patient's chest until a sufficient volume of ultrasound images are collected. The sonographer may collect the ultrasound images both with the ultrasound probe in a sagittal orientation and with the ultrasound probe in a transverse orientation. For example, the transverse orientation may be particularly beneficial in instances where a pulmonary pathology is detected. The collected images are stored in a central storage device (e.g., memory 118) and analyzed by the sonographer. The sonographer generates a set of measurements from the images (e.g., 50-100 records), and the images and measurements are collectively reviewed by a medical expert, such as a pulmonologist. The pulmonologist provides any clinical findings/conclusions in a report submitted to the patient's medical record.

As shown in FIG. 1, the ultrasound imaging system 100 includes a transmit beamformer 102, a transmitter 104, a probe 106, a receiver 110, and a receive beamformer 112.

The transmit beamformer 102 may be either a hardware beamformer or a software beamformer. In embodiments where the transmit beamformer 102 is a hardware beamformer, the transmit beamformer 102 may include one or more of a graphics processing unit (GPU), a microprocessor, a central processing unit (CPU), a digital signal processor (DSP), or any other type of processor capable of performing logical operations. The transmit beamformer 102 may be configured to perform conventional beamforming techniques as well as techniques such as retrospective transmit beamforming (RTB). Alternatively, in embodiments where the transmit beamformer 102 is a software beamformer, a processor (e.g., processor 116, as described below) may be configured to perform some or all of the functions associated with the transmit beamformer 102.

The probe 106 may be a linear array probe, a curvilinear array probe, a sector probe, or any other type of probe configured to obtain ultrasound data (e.g., B-mode data, color flow data, etc.). More specifically, the probe 106 may be any type of probe including a matrix transducer array (e.g., matrix configuration 300, as described below with reference to FIG. 3) configured to obtain three-dimensional (3D) ultrasound data. In some embodiments, the probe 106 may include a position sensor configured to detect a position of the probe 106 relative to one or more reference locations. That is, the position sensor may continuously track movement (e.g., rotation, translation, orientation, etc.) of the probe 106 relative to the location of the probe 106 when the anatomy being imaged is identified. For example, the anatomy being imaged may be identified as a pleura (e.g., represented by pleural line 710, as described below) at a first location of the probe 106. Then, the position sensor may track the movement of the probe 106 relative to the pleura in order to identify successive locations of the probe 106. In some embodiments, the position sensor may transmit position data to be stored within the ultrasound imaging system 100 (e.g., in memory 118).

The probe 106 may include a transducer configured to transmit and receive an ultrasound signal. In some embodiments, as shown in FIG. 1, the probe 106 includes signal elements 108. The signal elements 108 may be arranged in a transducer array, and in some embodiments may be arranged in a 2D array (e.g., as illustrated by the matrix configuration 300 shown in FIG. 3). As described herein, the 2D array of the signal elements 108 may allow for 3D ultrasound imaging (e.g., such that the transducer is configured to transmit and receive a 3D ultrasound signal). The transmit beamformer 102 and the transmitter 104 drive the signal elements 108 to emit pulsed ultrasonic signals into a body of a subject (e.g., a patient). For example, during a lung ultrasound, a sonographer or other clinician may navigate the probe 106 over a patient's chest so that the signal elements 108 in the probe 106 emit the pulsed ultrasonic signals into the patient's thoracic cavity. The pulsed ultrasonic signals are then back-scattered from anatomical structures in the body, such as blood cells or muscular tissues, to produce echoes that return to the signal elements 108. During a lung ultrasound, however, there is a mismatch in the acoustic impedance between the lung (e.g., due to the lung being full of air) and the material of the transducer, meaning the ultrasonic signals are unable to back-scatter from the air-filled lung. Rather, the ultrasonic signals back-scatter from the pleura (e.g., causing generation of the pleural line 710 in an ultrasound image of the lung, as described below with reference to FIG. 7).

The receiver 110 receives the echoes from the probe 106 and converts the echoes into electrical signals. The electrical signals are then passed through the receive beamformer 112, which produces the ultrasound data from the electrical signals. As described above with reference to the transmit beamformer 102, the receive beamformer 112 may be either a hardware beamformer or a software beamformer. In embodiments where the receive beamformer 112 is a hardware beamformer, the receive beamformer 112 may include one or more of a GPU, a microprocessor, a CPU, a DSP, or any other type of processor capable of performing logical operations. The receive beamformer 112 may be configured to perform conventional beamforming techniques as well as techniques such as retrospective transmit beamforming (RTB). Alternatively, in embodiments where the receive beamformer 112 is a software beamformer, a processor (e.g., processor 116, as described below) may be configured to perform some or all of the functions associated with the receive beamformer 112.

Although the transmit beamformer 102, the transmitter 104, the receiver 110, and the receive beamformer 112 are shown in FIG. 1 as being components of the ultrasound imaging system 100 that are distinct from the probe 106, it should be appreciated that in some embodiments, the probe 106 may include electronic circuitry configured to perform the functions of each of the transmit beamformer 102, the transmitter 104, the receiver 110, and/or the receive beamformer 112. That is, all or part of the transmit beamformer 102, the transmitter 104, the receiver 110, and/or the receive beamformer 112 may be situated within the probe 106.

Referring still to FIG. 1, the ultrasound imaging system 100 is shown to include a processing circuit 114. As shown, the processing circuit 114 may include at least one processor 116, a memory 118, an image processing circuit 120, an artificial intelligence (AI) circuit 122, and a control circuit 124. In this way, the processing circuit 114 may be structured or configured to execute or implement the instructions, commands, and/or control processes described herein with respect to the processor 116, the memory 118, the image processing circuit 120, the AI circuit 122, and the control circuit 124. While shown as being separate from the probe 106 in FIG. 1, it will be appreciated that the processing circuit 114 can be part of the probe 106. For example, the processing circuit 114 can be disposed in a handheld housing of the probe 106 (e.g., in the case of the probe 106 being a wireless probe).

The processor 116 may include a CPU, a GPU, a microprocessor, a DSP, a general-purpose single- or multi-chip processor, a field-programmable gate array (FPGA), or any other type of processor capable of performing logical operations. A general-purpose processor may be a microprocessor, or, any conventional processor, or state machine. A processor also may be implemented as a combination of computing devices, such as a combination of a DSP and a microprocessor, a plurality of microprocessors, one or more microprocessors in conjunction with a DSP core, or any other such configuration. In some embodiments, the processor 116 may be shared by multiple circuits (e.g., the circuits of the processor 116 may include or otherwise share the same processor which, in some example embodiments, may execute instructions stored, or otherwise accessed, via different areas of the memory 118). Alternatively or additionally, the processor 116 may be structured to perform or otherwise execute certain operations independent of one or more co-processors. In some embodiments, two or more processors may be coupled via a bus to enable independent, parallel, pipelined, or multi-threaded instruction execution. All such variations are intended to fall within the scope of the present disclosure.

The processor 116 may be configured to control the transmit beamformer 102, the transmitter 104, the receiver 110, and the receive beamformer 112. The processor 116 may also be in electronic communication with the probe 106. For purposes of this disclosure, the term "electronic communication" may be defined to include both wired and wireless communications.

In some embodiments, the processor 116 may be configured to control the probe 106 during data acquisition. That is, the processor 116 may control the data acquisition by controlling which of the signal elements 108 are active and by controlling a shape of the beam emitted from the probe 106. For example, using the matrix configuration 300 of the signal elements 108 shown in FIG. 3, the processor 116 may be configured to control a scanning plane of the probe 106 such that data is acquired from a sagittal plane (e.g., azimuth plane 210), an elevation plane (e.g., elevation plane 215), and/or a transverse plane (e.g., mid-rib-space transverse plane 805, pathology-centered transverse plane 810) within a field of view of the probe 106. According to other embodiments, the scanning plane of the probe 106 may be controlled by another component of the ultrasound imaging system 100 (e.g., the control circuit 124).

Alternatively or additionally, the processor 116 may include a complex demodulator configured to demodulate radio frequency (RF) data obtained by the probe 106 and generate raw data. According to other embodiments, the demodulation of the RF data may be performed by another component of the ultrasound imaging system 100. The processor 116 may perform the processing operations described herein according to a plurality of selectable ultrasound modalities.

Depending on a mode of operation of the ultrasound imaging system 100, the processor 116 may process ultrasound data obtained by the probe 106 according to the mode of operation to generate image data. For example, the mode of operation may include B-mode, color flow Doppler mode, M-mode, color M-mode, spectral Doppler, elastography, TVI, strain, strain rate, and the like. Various of these modes of operation may be configured to, for instance, convert ultrasound data from beam space coordinates (e.g., received from the receive beamformer 112) to display space coordinates (e.g., such that the ultrasound data may be displayed as image data). In some embodiments, the mode of operation may allow for video processing by the processor 116 such that a series of images (e.g., processed ultrasound data) may be displayed in real-time while a scanning session/procedure is being performed on a patient. An operator of the ultrasound imaging system 100 (e.g., a sonographer) may switch between various modes in order to obtain a variety of ultrasound data and to perform a complete scan of an anatomical region of interest. For example, the operator may switch between modes using user interface 130 (e.g., using physical controls, interface inputs representing physical controls, etc.).

The processor 116 performs the processing operations in real-time as the echo signals are received by the receiver 110 from the probe 106. For the purposes of this disclosure, the term "real-time" is defined to include a procedure that is performed without any intentional delay. As an illustrative, non-limiting example, in certain instances, the ultrasound imaging system 100 may obtain images at a real-time volume-rate of 7-20 volumes/sec. It should be appreciated, however, that the real-time volume-rate may be dependent on the length of time that it takes to obtain each volume of data for display. Thus, the ultrasound imaging system 100 may be configured to obtain 2D data of an anatomical region at a faster rate than 3D data of the same anatomical region because it takes longer to obtain a volume of 3D data than the same volume of 2D data. Similarly, when the ultrasound imaging system 100 obtains a relatively large volume of data, the real-time volume-rate may be slower than for a smaller volume of data. For example, during an abdominal scan, the real-time volume-rate may be slower if the patient is an adult versus if the patient is an infant because the volume of data is larger for the adult than for the infant (e.g., due to the abdomen of an adult being larger than the abdomen of an infant). Therefore, certain implementations of the ultrasound imaging system 100 may have real-time volume-rates that are faster than 20 volumes/sec, while other implementations of the ultrasound imaging system 100 may have real-time volume-rates that are slower than 7 volumes/sec.

In some embodiments, the ultrasound imaging system 100 may include multiple processors configured to perform the processing operations/functionality described with reference to processor 116. For example, in such embodiments, a first processor of the multiple processors may be configured to demodulate and decimate the RF signal while a second processor of the multiple processors may be configured to further process the RF data prior to displaying an image representative of the data. It should be appreciated that other embodiments may use a different arrangement of processors.

The processor 116 may also be in electronic communication with the display device 132 such that the processor 116 may process ultrasound data obtained by the probe 106 and generate images to display on the display device 132 (e.g., ultrasound image 700, first ultrasound image 900*a*, second ultrasound image 900*b*, first ultrasound image 1000*a*, and/or second ultrasound image 1000*b* as described below with reference to FIGS. 7 and 9A-10B).

As shown in FIG. 1, the processing circuit 114 also includes the memory 118. The memory 118 may be configured to, for example, store processed volumes of data obtained by the ultrasound imaging system 100 (e.g., ultrasound data collected by the probe 106). For example, the memory 118 may be a hospital picture archiving and communication system (PACS). The memory 118 (e.g., memory, memory unit, storage device, etc.) may include one or more devices (e.g., RAM, ROM, Flash memory, hard disk storage, etc.) for storing data and/or computer code for completing or facilitating the processes, layers, and modules described in the present application. The memory 118 may be or include tangible, non-transient volatile memory or non-volatile memory. The memory 118 may also include database components, object code components, script components, or any other type of information structure for supporting the activities and information structures described in the present application.

In various embodiments, the memory 118 may have varying capacity (e.g., storage space) across embodiments of the ultrasound imaging system 100. For example, the memory 118 may be configured to store at least 60 minutes'worth of ultrasound data. The ultrasound data may be stored in the memory 118 such that the ultrasound data may be retrieved according to an order/time of acquiring the data. That is, the ultrasound data may be stored with a timestamp indicating a time at which the ultrasound data was collected and may be retrieved starting with an oldest time at which the ultrasound data was collected.

The processing circuit 114 also includes the image processing circuit 120, the AI circuit 122, and the control circuit 124. Each of the image processing circuit 120, the AI circuit 122, and the control circuit 124 are configured to facilitate automating bi-plane ultrasound imaging using the probe 106 during an ultrasound scan.

The image processing circuit 120 is configured to analyze ultrasound image data (e.g., obtained using the probe 106, stored in the memory 118, etc.) and identify anatomical structures, scanning planes, pathologies, and/or other features depicted by/contained within the image data. In some instances, the image processing circuit 120 may include multiple deep learning-based models configured to analyze the image data. Alternatively or additionally, the image processing circuit 120 may use multiple deep learning-based models included in the AI circuit 122 to analyze the image data, as described herein.

In some embodiments, the image processing circuit 120 may be configured to identify an anatomical structure, feature, region, etc. captured by the image data. For example, during a lung ultrasound, the image processing circuit 120 may be configured to identify the pleura, rib bones, shadows of the rib bones, and/or other pulmonary structures/features/regions depicted in the image data. The image processing circuit 120 may be configured to identify the anatomical structure using one or more algorithms (e.g., image processing algorithms such as edge detection, machine learning models, deep neural networks, etc.). In some embodiments, the image processing circuit 120 may be configured to apply one or more algorithms used by the AI circuit 122 and/or retrieved from the external database 128. For example, as described below with reference to FIGS. 5, 6A, and 6B, the image processing circuit 120 may use one or more algorithms to assess a rib space (e.g., using linear regression to estimate rib edge lines) captured by the image data. In this way, the image processing circuit 120 may be configured to estimate a curvature of the ribs, and the scanning plane of the probe 106 may be adjusted based on the estimated curvature such that the rib bones do not interfere with an ultrasound image of a lung, as described herein.

In some embodiments, the image processing circuit 120 may identify anatomical features such as bones, blood vessels, organs, etc., based on a shape, relative proximity, apparent depth, orientation, etc. of said features in the image data. Then, based on the identified anatomical features, the image processing circuit 120 may be configured to determine the anatomical structure depicted in the image data. For example, because a lung is not able to be imaged directly (e.g., due to the lung being full of air and the mismatch in the acoustic impedance between the air and the transducer of the probe 106), the image processing circuit 120 may determine that the lung is being imaged based on a movement and/or orientation of the lung relative to surrounding structures, such as the pleura, via a deep learning classification model trained to recognize the movement and/or orientation of the lung, and other anatomical structures. In some embodiments, the image processing circuit 120 may detect movement of structures in the image data by comparing the location, shape, size, etc., of identified structures across a set of images (e.g., a cine loop).

According to some embodiments, the image processing circuit 120 may be configured to identify a view or a scanning plane from which the ultrasound data is obtained. For example, the image processing circuit 120 may be configured to identify whether the image data depicts a sagittal view (e.g., along azimuth plane 210) and/or a transverse view (e.g., along at least one of mid-rib-space transverse plane 805, pathology-centered transverse plane 810, etc.).

The image processing circuit 120 may also be configured to determine the presence of a pathology (e.g., an injury, disease, abnormality, etc.) in the image data. In some embodiments, the image processing circuit 120 may use a deep learning classification model trained to recognize various pathologies in the anatomical structure represented by the image data to specify the pathology that is present. Continuing with the example of the lung ultrasound, the image processing circuit 120 may use a deep learning classification model trained to recognize pulmonary pathologies to determine whether a pathology is present in the image data from the lung ultrasound. For instance, the image processing circuit 120 may identify pleural effusion (e.g., a buildup of fluid) in the pleura as a pulmonary pathology present in the image data. In some embodiments, the AI circuit 122 may be configured to perform any of the functions of the image processing circuit 120 described herein using multiple deep learning-based models configured to analyze the image data.

Based on the analysis of the image data, processing circuit 114 (e.g., the AI circuit 122) may be configured to determine an adjustment to the probe 106. In some embodiments, the adjustment to the probe 106 may include a change in the scanning plane of the probe 106. For example, during a lung ultrasound, the image processing circuit 120 may identify estimated rib edge lines (e.g., using a plurality of images obtained from a plurality of sagittal planes, such as from the plurality of sagittal planes 605, and linear regression, as described below), and the processing circuit 114 may determine, as described below with reference to step 510 of method 500, a mid-rib-space transverse view to which the scanning plane of the probe 106 is adjusted (e.g., mid-rib-space transverse plane 805). As another example, the image processing circuit 120 may identify a pathology (e.g., pathology 815) within the image data, and the processing circuit 114 may determine, as described below with reference to FIG. 8B, a pathology-centered transverse view to which the scanning plane of the probe 106 is adjusted (e.g., pathology-centered transverse plane 810). In this way, the pathology may be more accurately imaged due to bi-plane images (e.g., from the sagittal view and from the transverse view) obtained by the probe 106 being centered around a location of the pathology (e.g., such that an intersection of the azimuth plane 210 and the pathology-centered transverse plane 810 is at the location of the pathology, as shown in FIG. 8B).

In some embodiments, the processing circuit 114 (e.g., the AI circuit 122) may be configured to automatically generate a control signal prompting an adjustment of the probe 106 based on the analysis of the image data performed by the image processing circuit 120. The control signal may be received by the control circuit 124, which may be configured to automatically align the scanning plane of the probe 106 such that the probe 106 is configured to acquire image data according to the scanning plane prescribed by the control signal (e.g., a sagittal plane, a transverse plane, etc.). For example, the control signal may prompt the control circuit 124 to switch the scanning plane of the probe 106 from a sagittal plane to a transverse plane. As another example, the control signal may prompt the control circuit 124 to switch the scanning plane of the probe 106 from a mid-rib-space transverse view (e.g., the mid-rib-space transverse plane 805) to a pathology-centered transverse view (e.g., the pathology-centered transverse plane 810) upon detection of a pathology within the image data.

The ultrasound imaging system 100 may also include an external database 128 and a user interface 130. The external database 128 refers to a database from which the processing circuit 114 (e.g., the image processing circuit 120, the AI circuit 122) retrieves information used in automating bi-plane imaging during a lung ultrasound. For example, the external database 128 may be a medical information data-base. The medical information database may store clinical guidelines, standard practices, medical literature, medical textbooks, published research, previous case studies, and so on. Depending on an implementation of the ultrasound imaging system 100 and/or a procedure performed thereby, the processing circuit 114 may retrieve clinical guidelines, standard practices, medical literature, medical textbooks, published research, and previous case studies related to the implementation and/or procedure. For example, if the ultra-sound imaging system 100 is being used in a hospital setting to conduct a lung ultrasound, the processing circuit 114 may retrieve clinical guidelines and standard practices related to the hospital setting and the lung ultrasound. Continuing with this example, the processing circuit 114 may also retrieve information from the medical literature, medical textbooks, published research, and previous case studies related to pulmonary anatomy and the lung ultrasound. In some instances, as described with reference to FIGS. 5, 6A, and 6B, the information retrieved from the external database 128 may include one or more algorithms used to estimate rib edge lines in an ultrasound image of a lung.

The user interface 130 may be used by a sonographer or other clinician to control operation of the ultrasound imaging system 100. For example, the sonographer may use the user interface 130 to control the input of patient data, to change a scanning or display parameter, and/or to select various other modes, operations, parameters, etc. of the ultrasound imaging system 100. In some embodiments, the user interface 130 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. Alternatively, in other embodiments, the user interface 130 may be an electronic device that was designed and developed for use in a medical environment.

According to some embodiments, the user interface 130 may be physically separate from the rest of the ultrasound imaging system 100 (e.g., the transmit beamformer 102, the transmitter 104, the probe 106, the receiver 110, the receive beamformer 112, the processing circuit 114, and/or the external database 128). The user interface 130 may communicate with the processor 116 through a wireless protocol, such as Wi-Fi, Bluetooth, wireless local area network (WLAN), near-field communication, and so on. According to some embodiments, the user interface 130 may communicate with the processor 116 through an application programming interface (API).

In some embodiments, the user interface 130 may include physical controls such as one or more of buttons, sliders, a rotary knob, a mouse, a keyboard, a trackball, hard keys linked to specific actions, soft keys that may be configured to control different functions, and so on. As shown in FIG. 1, the user interface 130 may also include a display device 132. In some embodiments, the display device 132 may be configured to display a graphical user interface (GUI) based on an instruction from the memory 118. The GUI may include user interface icons representing commands and instructions relating to the operation of the ultrasound imaging system 100. The user interface icons of the GUI may be configured such that a user (e.g., the sonographer, clinician, etc.) may select a specific user interface icon in order to initiate a specific function controlled by the GUI. For example, various user interface icons may be used to represent windows, menus, buttons, cursors, scroll bars, and so on. That is, the physical controls of the user interface 130 may be included as individual hardware elements, as user interface icons displayed on the display device 132, or as a combination of hardware elements and user interface icons.

In some embodiments, the display device 132 may include a touch-sensitive display device or a touch screen. According to such embodiments, the touch screen may be configured to interact with the GUI displayed by the display device 132 such that a user (e.g., the sonographer) can interact with the GUI via the touch screen. The touch screen may be a single-point touch screen that is configured to detect a single contact point at a time, or the touch screen may be a multi-point touch screen that is configured to detect multiple points of contact at a time. For embodiments where the touch screen is a multi-point touch screen, the touch screen may be configured to detect multi-point gestures involving contact from two or more of a user's fingers at a time. The touch screen may be a resistive touch screen, a capacitive touch screen, or any other type of touch screen that is configured to receive inputs from a stylus or one or more of a user's fingers. According to some embodiments, the touch screen may be an optical touch screen that uses technology such as infrared light or other frequencies of light to detect one or more points of contact initiated by a user. In some embodiments, the touch screen may be incorporated as part of the display device 132 or may be separate from the display device 132. The user interface 130 may also include a proximity sensor configured to detect objects and/or gestures that are within a predetermined distance (e.g., five feet, six inches, ten centimeters, etc.) of the proximity sensor. In various embodiments, the proximity sensor may be located on the display device 132 or as part of a touch screen that is separate from the display device 132.

Figure 2:
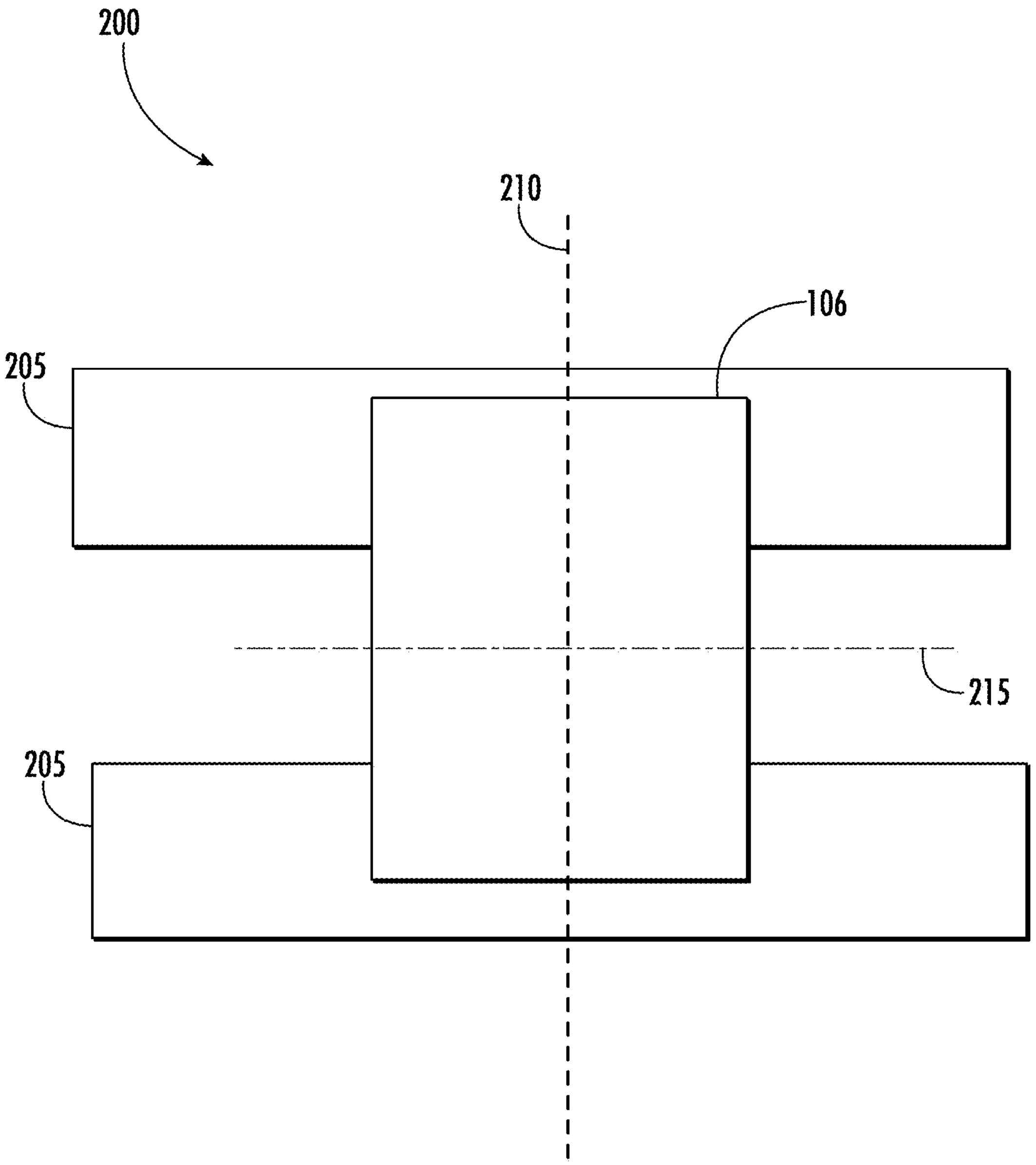
FIG. 2 is a diagram of a desired orientation of an ultrasound probe used in the ultrasound imaging system of FIG. 1, according to an example embodiment.

Referring to FIG. 2, an orientation 200 of the probe 106 is shown. The orientation 200 shown in FIG. 2 refers to a desired orientation of the ultrasound probe 106 during a lung ultrasound, as described herein. More specifically, the orientation 200 refers to an orientation of the probe 106 relative to ribs 205 (e.g., shown as an upper rib bone and a lower rib bone, where the upper rib bone is proximate to a patient's head and the lower rib bone is proximate to a patient's feet).

As shown, the orientation 200 may be defined by two orthogonal planes including an azimuthal plane 210 and an elevation plane 215. The azimuthal plane 210 captures image data from a sagittal view of the ultrasound probe 106, and the elevation plane 215 captures image data from a transverse view of the ultrasound probe 106. According to the orientation 200, the azimuthal plane 210 is shown perpendicular to the ribs 205, and the elevation plane 215 is shown parallel to the ribs 205. Therefore, during a lung ultrasound, it may be desired to orient the probe 106 such that the azimuthal plane 210 lies across (e.g., perpendicular to) a direction of the ribs 205 and the elevation plane 215 lies along (e.g., parallel to) the direction of the ribs 205.

In practice, however, a sonographer may not be able to orient the ultrasound probe 106 such that the azimuthal plane 210 lies perpendicular to the ribs 205 and the elevation plane 215 lies parallel to the ribs 205 due to a curvature of a patient's ribs. In other words, the patient's ribs are not exactly perpendicular to the sagittal view, as suggested by FIG. 2, but rather, follow a curvature (e.g., as represented in FIGS. 6A-6B and 8A-8C). Therefore, when a sonographer places the probe 106 in a sagittal orientation (e.g., with an indicator pointed towards the patient's head) during a lung ultrasound, the azimuthal plane 210 is not perpendicular to the ribs 205, as desired and as shown in FIG. 2, due to the curvature/direction of the patient's ribs. Moreover, the curvature of the patient's ribs may be unique to an individual anatomy of the patient, meaning the curvature of a first patient's ribs may differ from a curvature of a second patient's ribs, and so on. Rather than relying on the expertise/skill of the sonographer to orient the probe 106 such that the azimuthal plane 210 is perpendicular to the ribs 205 and the elevation plane 215 is parallel to the ribs 205, the scanning plane of the probe 106 may be automatically adjusted, as described herein, such that the probe 106 is configured to capture ultrasound images from a transverse view between the patient's ribs (e.g., the mid-rib-space transverse plane 805, the pathology-centered transverse plane 810).

Figure 3:
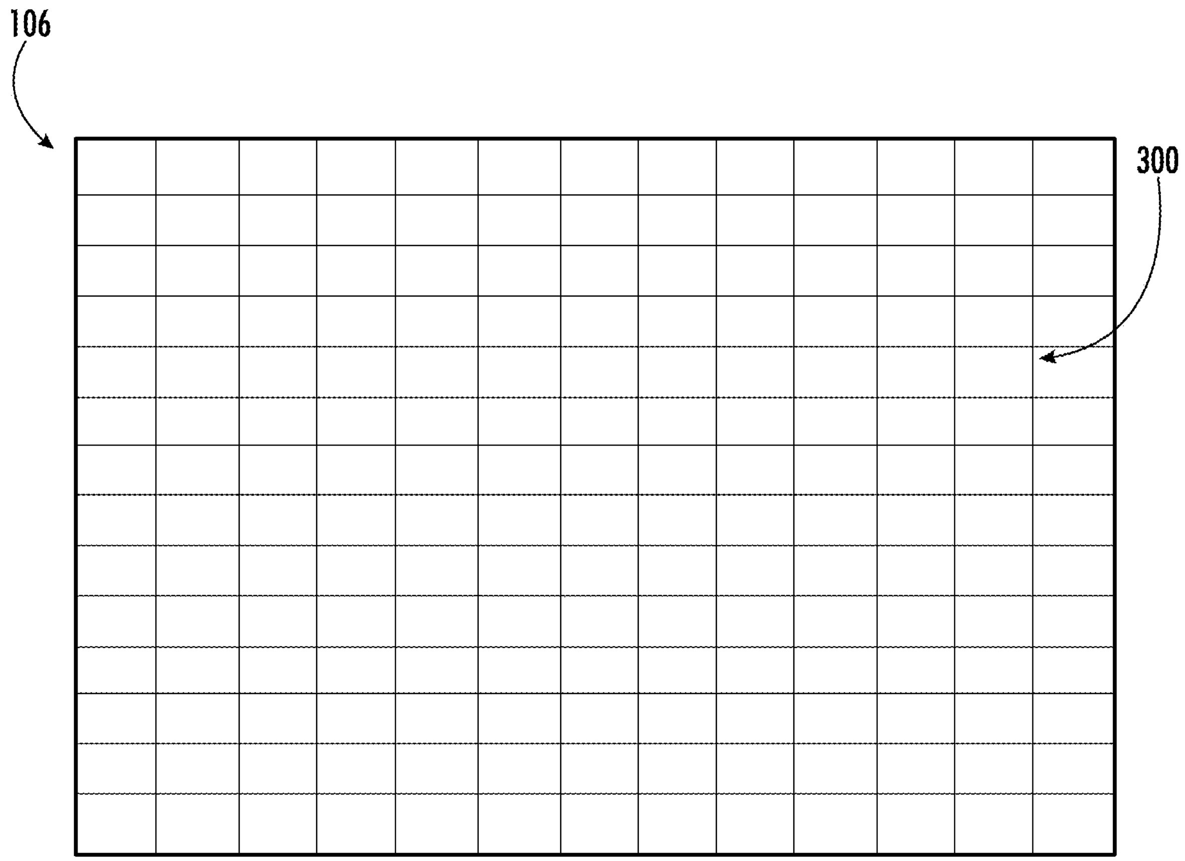
FIG. 3 is an illustration of a configuration of the ultrasound probe used in the ultrasound imaging system of FIG. 1, according to an example embodiment.

Referring to FIG. 3, a matrix configuration 300 of the ultrasound probe 106 is shown. The matrix configuration 300 refers to a configuration of the signal elements 108 within the ultrasound probe 106. More specifically, the matrix configuration 300 may include a 2D array of the signal elements 108 such that the probe 106 is configured to capture image data from several planes (e.g., a sagittal plane, an elevation plane, a transverse plane, etc.). In other words, with the matrix configuration 300, the probe 106 may obtain ultrasound images from a plurality of scanning planes. More specifically, as described herein, the probe 106 may be configured to obtain ultrasound images of a patient's lung from a sagittal scanning plane, an elevation scanning plane, and/or a transverse scanning plane. According to an example configuration of the probe 106, the matrix configuration 300 may include a 2D array of 6,000 elements (e.g., signal elements 108).

Therefore, using the matrix configuration 300, the ultrasound probe 106 may be configured to capture ultrasound data from a transverse view that lies between and is parallel with the ribs 205, as described above with reference to the desired orientation (e.g., orientation 200) of the ultrasound probe 106 depicted in FIG. 2. That is, the transverse view refers to a third plane, in addition to the azimuthal plane 210 and the elevation plane 215, from which the probe 106 is configured to capture image data. As described herein, with the matrix configuration 300, the scanning plane of the probe 106 may be adjusted to match the curvature of the ribs 205 (e.g., determined using method 500, as described below with reference to FIGS. 5, 6A, and 6B). In other words, although the azimuthal plane 210 is not perpendicular to the ribs 205 and the elevation plane 215 is not parallel to the ribs 205, the matrix configuration 300 allows the probe 106 to capture image data from a scanning plane that is parallel with the ribs 205 (e.g., the traverse view) based on the anatomy of the patient being imaged during the lung ultrasound.

Figure 4:
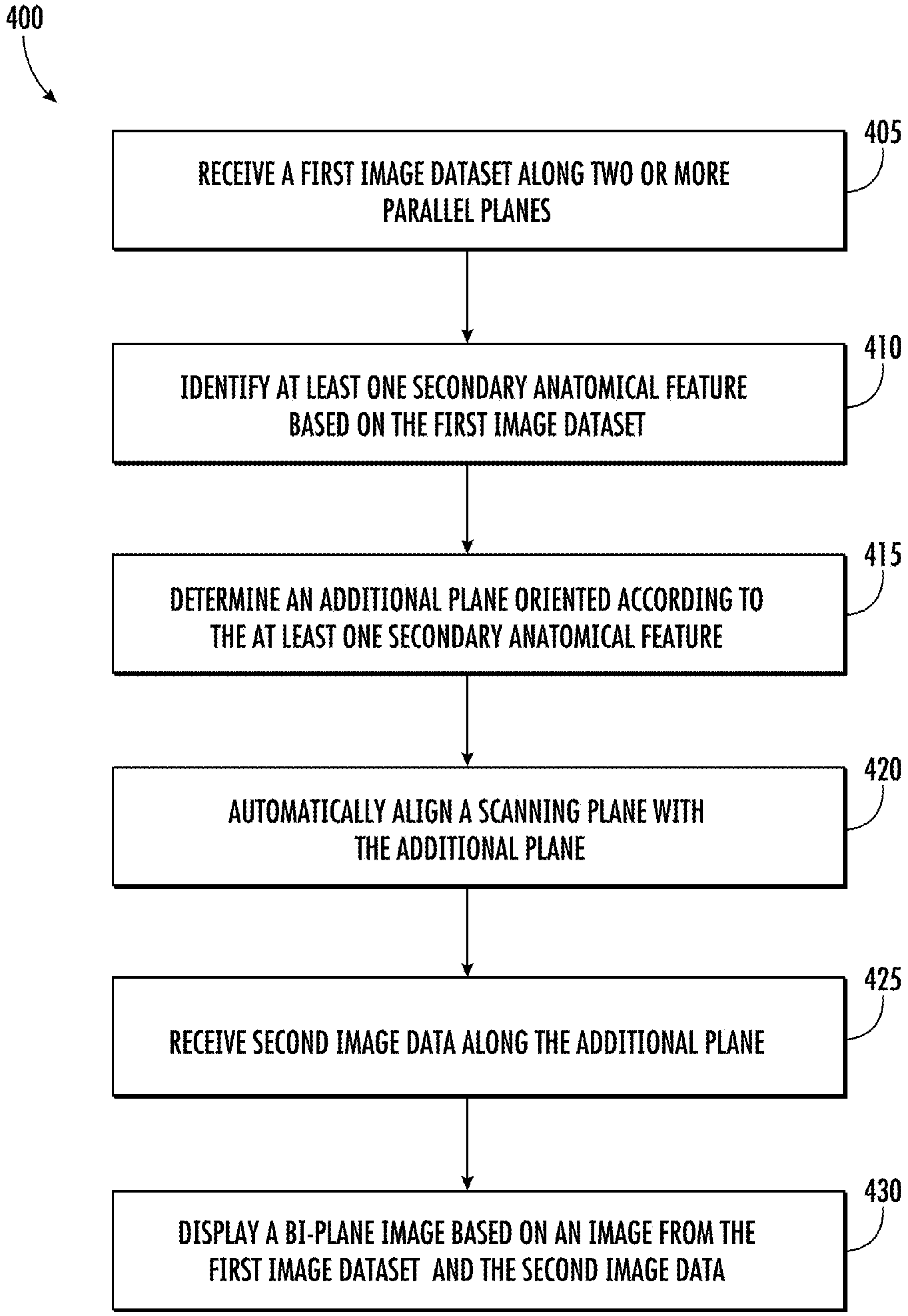
FIG. 4 is a flow chart illustrating a method for automating bi-plane ultrasound imaging using the ultrasound imaging system of FIG. 1, according to an example embodiment.

Referring to FIG. 4, a flow chart illustrating a method 400 for automating bi-plane ultrasound imaging using an ultrasound imaging system is shown. In at least one embodiment, the ultrasound imaging system referred to by method 400 is the ultrasound imaging system 100 described above with reference to FIG. 1, and method 400 may be implemented by the ultrasound imaging system 100. In some embodiments, method 400 may be implemented as executable instructions in a memory of the ultrasound imaging system 100, such as the memory 118 of FIG. 1.

Figure 6A:
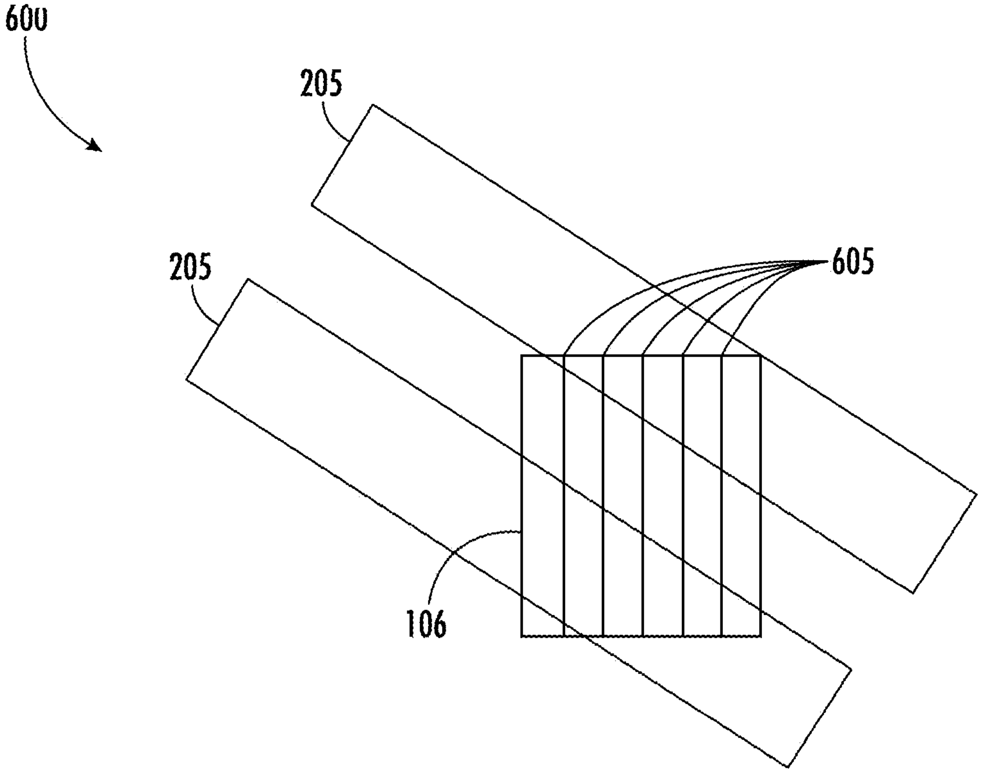
FIG. 6A is a first diagram illustrating of the method of FIG. 5, according to an example embodiment.
Figure 6B:
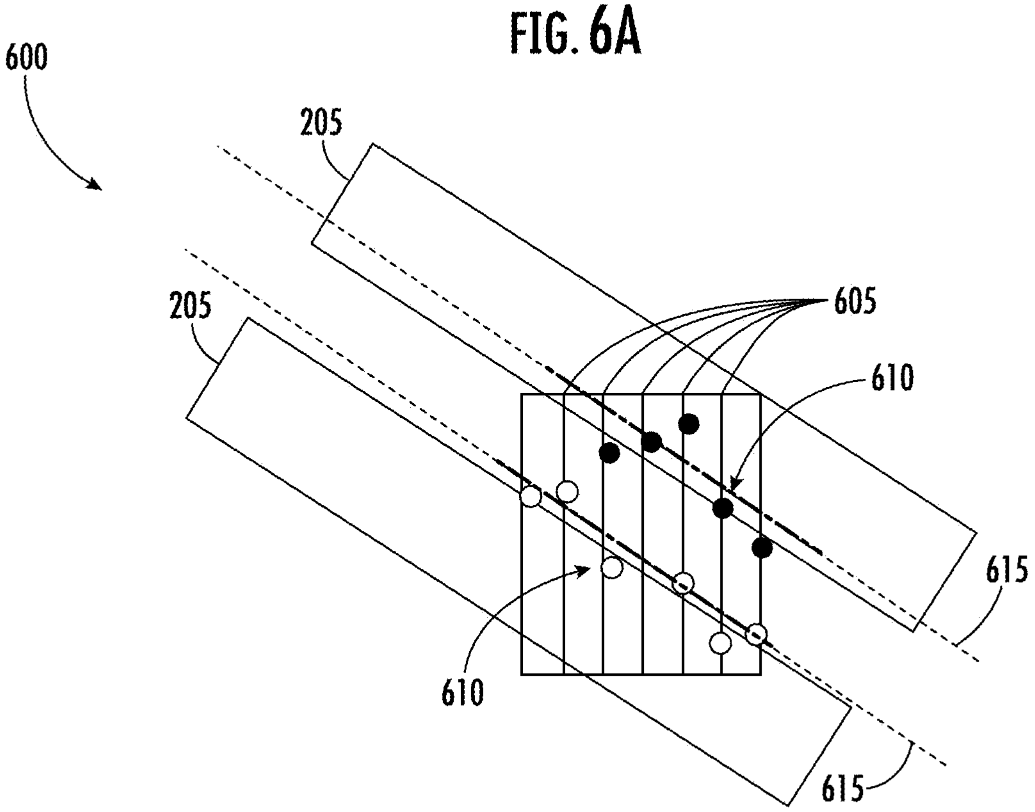
FIG. 6B is a second diagram illustrating of the method of FIG. 5, according to an example embodiment.

As shown in FIG. 4, at step 405, method 400 may include receiving a first image dataset along two or more parallel planes of a first orientation in a field of view of an ultrasound probe. In some embodiments, and as described herein, the first orientation may refer to a sagittal plane. The first image dataset may be obtained by the ultrasound probe 106 (e.g., using the matrix configuration 300) and may be received by the image processing circuit 120. In some embodiments, the two or more parallel planes are depicted by the plurality of sagittal planes 605, as shown in FIGS. 6A and 6B. In some embodiments, the first image dataset may include two or more ultrasound images representing a primary anatomical feature being imaged. For example, as described herein, the first image dataset may be obtained during a lung ultrasound, and therefore the primary anatomical feature may include a lung of the patient being imaged. It should be appreciated, however, that although the ultrasound imaging system 100 cannot capture an image of the lung due to the lung being filled with air, an image of the lung may be derived using surrounding anatomical structures/features (e.g., ribs 205, a pleural line 710, etc.) depicted in the first image dataset. In some embodiments, step 405 may also include detecting a pathology (e.g., pathology 815, as shown in FIG. 8B) in the first image dataset (e.g., using the image processing circuit 120, as described above).

Step 410 of method 400 includes identifying at least one secondary anatomical feature based on the first image dataset. In some embodiments, step 410 may be performed by the image processing circuit 120, as described above. The at least one secondary anatomical feature identified from the first image dataset may refer to two rib bones (e.g., ribs 205). That is, the at least one secondary anatomical feature identified from the first image dataset (e.g., the ribs 205) may be obstructing a view of the primary anatomical feature (e.g., the lung).

At step 415, method 400 includes determining an additional plane oriented according to the at least one secondary anatomical feature within the field of view of the ultrasound probe 106. For example, the additional plane may be a transverse plane parallel to the at least one secondary anatomical feature. That is, according to various embodiments described herein, the transverse plane refers to a scanning plane that is parallel to the direction of the ribs 205. In some embodiments, the transverse plane may be determined using method 500, as described below with reference to FIGS. 5, 6A, and 6B. Although the transverse plane (e.g., the scanning plane that is parallel to the direction of the ribs 205) may be depicted as the elevation plane 215 in FIG. 2 (e.g., where there is no curvature of the ribs 205), the transverse plane determined using the curvature of the ribs 205 (e.g., the at least one secondary anatomical feature identified at step 410) is depicted by the mid-rib-space transverse plane 805 and/or the pathology-centered transverse plane 810 shown in FIGS. 8A-8C. In some embodiments, where there is a pathology detected in the first image dataset at step 405, the transverse plane may be determined at step 415 such that the transverse plane parallel to the at least one secondary anatomical feature intersects a location of the pathology (e.g., the pathology-centered transverse plane 810), as shown in FIG. 8B.

Method 400 continues at step 420 by automatically aligning a scanning plane of the ultrasound probe with the additional plane determined at step 415. In some embodiments, the control circuit 124 may be configured to automatically align the scanning plane of the ultrasound probe 106 based on a control signal, as described above with reference to FIG. 1. That is, automatically aligning the scanning plane at step 420 may include controlling which of the signal elements 108 included in the matrix configuration 300 are active such that the active signal elements 108 from the matrix configuration 300 are configured to collect ultrasound data along the additional plane (e.g., a transverse plane parallel to the ribs 205) determined at step 415.

Alternatively or additionally, in some embodiments, step 420 may include providing an instruction to a user (e.g., the sonographer performing the lung ultrasound) regarding how to adjust the scanning plane of the ultrasound probe 106 such that the scanning plane is aligned with the additional plane. For example, the instruction could prompt the user to rotate the probe 106 counterclockwise by X degrees or clockwise by Y degrees such that the rotation of the probe 106 results in alignment of the scanning plane with the additional plane determined at step 415.

After aligning the scanning plane with the additional plane at step 420, method 400 includes receiving second image data along the additional plane at step 425. The second image data refers to image data obtained by the probe 106 when the scanning plane of the probe 106 (e.g., defined by activation of the signal elements 108 in the matrix configuration 300) is aligned with the additional plane (e.g., a transverse plane) oriented according to the at least one secondary anatomical feature (e.g., the ribs 205). In some embodiments, where the primary anatomical feature being imaged is a lung, the second image data may be obtained by the probe 106 according to a frequency of a breathing cycle of the patient from whom the first image dataset and the second image data is obtained.

At step 430, a bi-plane image based on an image from the first image dataset (e.g., received at step 405) and the second image data (e.g., received at step 425) is displayed. In some embodiments, the bi-plane image refers to a 3D ultrasound image depicting ultrasound data obtained from the sagittal view (e.g., along the azimuthal plane 210) and from the transverse view (e.g., along at least one of the mid-rib-space transverse plane 805 or the pathology-centered transverse plane 810 shown in FIGS. 8A-8C). In some embodiments, the bi-plane image may be displayed via the display device 132. Although the systems and methods described herein refer to exemplary embodiments in which the two or more parallel planes refer to sagittal planes and the additional plane refers to a transverse plane, it should be appreciated that this disclosure is not limited to such operation and that the various systems and methods are configured to apply to any variety of planes and/or orientations.

Figure 5:
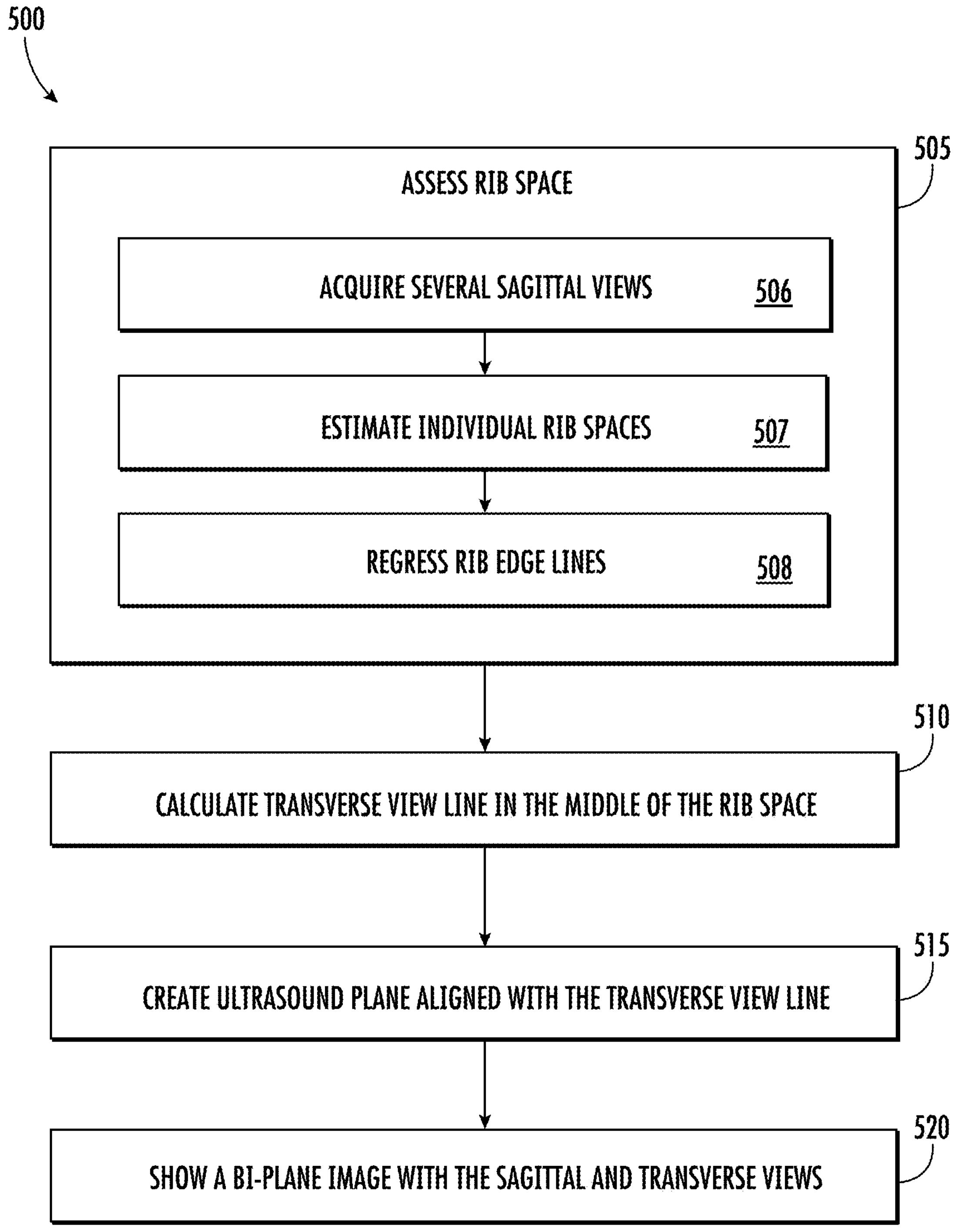
FIG. 5 is a flow chart illustrating a method for assessing an anatomical region during the method of FIG. 4, according to an example embodiment.

Referring to FIG. 5, a flow chart is shown illustrating a method 500 for determining an orientation of an ultrasound probe during the method 400. In at least one embodiment, the ultrasound probe referred to by method 500 is the ultrasound probe 106 described above with reference to FIG. 1, and method 500 may be implemented by the ultrasound imaging system 100. In some embodiments, method 500 may be implemented as executable instructions in a memory of the ultrasound imaging system 100, such as the memory 118 of FIG. 1.

As shown in FIG. 5, method 500 may include assessing a rib space at step 505. In some embodiments, step 505 of method 500 may be performed upon completion of step 410 of method 400 (e.g., identifying the at least one secondary anatomical feature based on the first image dataset). That is, upon identification of the ribs 205 from the first image dataset, the ribs 205 and a surrounding anatomical region may be assessed in order to determine the transverse plane parallel to the at least one secondary anatomical features at step 415.

In some embodiments, assessing the rib space at step 505 may include acquiring several sagittal views at step 506. The several sagittal views acquired at step 506 refer to several azimuthal-oriented planes (e.g., along several azimuthal planes such as the azimuthal plane 210) from which ultrasound data is collected by the probe 106. For example, the several sagittal views may refer to the plurality of sagittal views 605, as shown in FIGS. 6A and 6B. In some instances, the several sagittal views acquired at step 506 refer to the one or more sagittal planes of the first image dataset received at step 405 of method 400.

Figure 7:
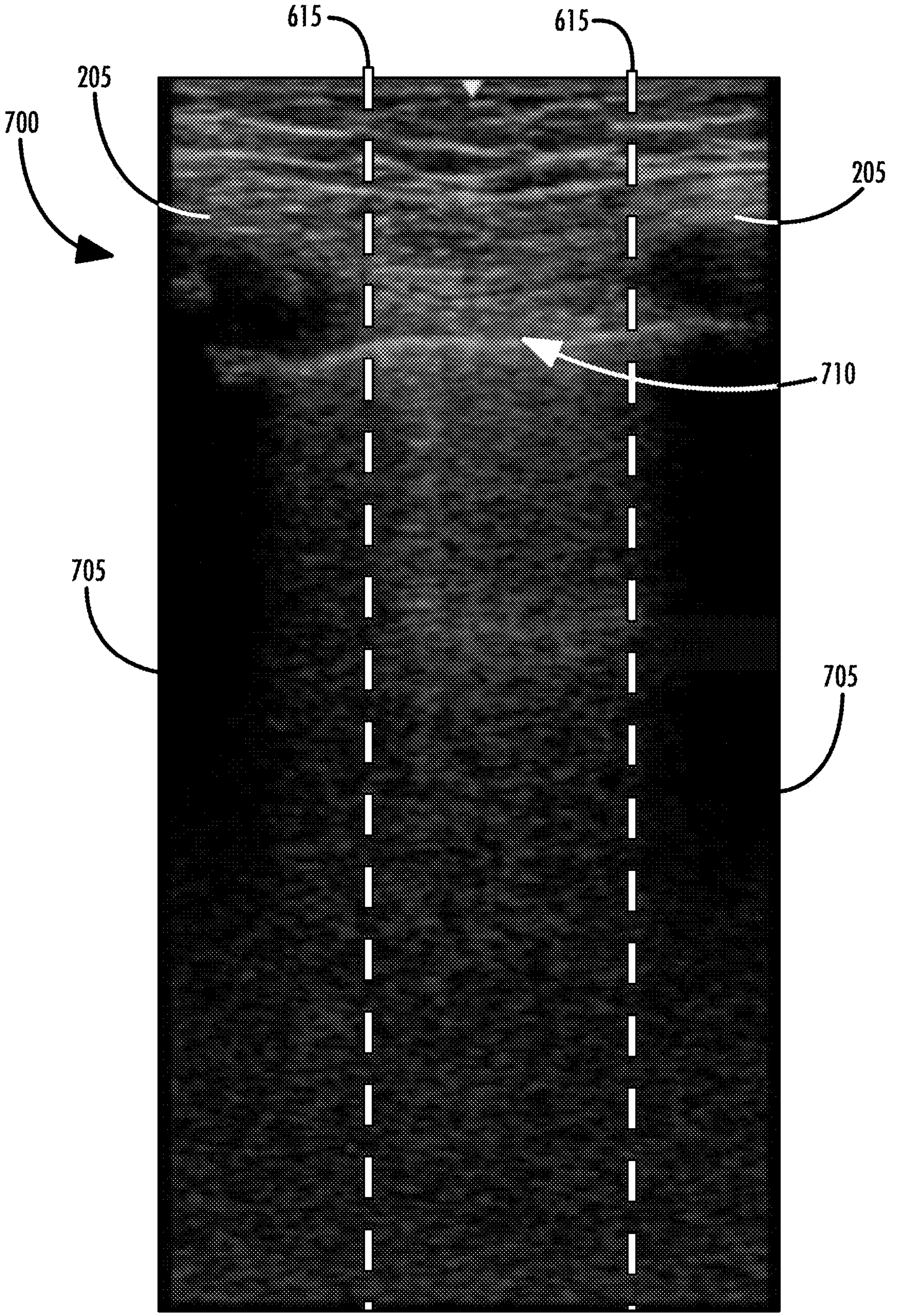
FIG. 7 is an illustration of an analysis of an ultrasound image using the method of FIG. 5, according to an example embodiment.

After acquiring the several sagittal views at step 506, assessing the rib space at step 505 may include estimating individual rib spaces at step 507. That is, the individual rib spaces may refer to a space, gap, distance, etc., between two consecutive rib bones (e.g., a space between the ribs 205). The space between the ribs 205 may be estimated (e.g., measured) using the several sagittal views acquired at step 506. Then, based on the estimated individual rib spaces from step 507, assessing the rib space at step 505 may include regressing rib edge lines at step 508. That is, the processing circuit 114 (e.g., the image processing circuit 120, the AI circuit 122) may be configured to regress one or more edge lines (e.g., regression lines 615, as shown in FIGS. 6B and 7) of the ribs 205, as described below with reference to FIGS. 6A and 6B. The rib edge lines may be used to represent the curvature of the ribs 205.

As shown in FIG. 5, after assessing the rib space at step 505, method 500 may continue by calculating a transverse view line in the middle of the rib space (e.g., shown as mid-rib-space transverse plane 805 in FIGS. 8A and 8C) at step 510. In some embodiments, the transverse view line calculated at step 510 is the transverse plane determined at step 415 of method 400. The transverse view line calculated at step 510 refers to a line between the ribs 205 and parallel with the direction of the ribs 205. In other words, the transverse view line may be calculated using the individual rib space estimated at step 507 and based on a direction of the rib edge lines regressed at step 508. In some embodiments, calculating the transverse view line at step 510 may include calculating a midpoint of the space between the ribs 205 (e.g., the space estimated at step 507).

At step 515, an ultrasound plane aligned with the transverse view line is created. That is, the ultrasound plane created at step 515 may be the scanning plane automatically aligned with the transverse plane at step 420 of method 400. As described above, the ultrasound plane may be created by activating specific signal elements 108 within the matrix configuration 300 such that the active signal elements 108 are configured to capture ultrasound data along the transverse view line calculated at step 510. In some embodiments, where a pathology (e.g., pathology 815) is detected in the first image dataset, the ultrasound plane created at step 515 may be shifted from the middle of the rib space such that that ultrasound plane intersects a location of the pathology.

After creating the ultrasound plane at step 515, a bi-plane image with sagittal (e.g., from the several sagittal views acquired at step 506) and transverse (e.g., from the transverse view line calculated at step 510) is shown at step 520. In some embodiments, the bi-plane image shown at step 520 is the bi-plane image displayed at step 430 of method 400, as described above.

Referring to FIGS. 6A-6B, an orientation 600 of the ultrasound probe 106 relative to the ribs 205 is shown. The orientation 600 refers to an orientation of the ultrasound probe 106 used to assess the ribs 205 and a space between the ribs 205 (e.g., as described above with reference to method 500 of FIG. 5). As described therein, assessing the ribs 205 includes receiving a plurality of sagittal planes 605.

Then, referring to FIG. 6B, intersections between each of the plurality of sagittal planes 605 and an edge of each of the ribs 205 are marked with a plurality of regression points 610. In some instances, the regression points 610 may include outliers and/or missing intersection points. The regression points 610 are used in generating the regression lines 615. The regression lines 615 refer to an estimation of the edge of the ribs 205 based on the intersections between each of the plurality of sagittal planes 605 and the edge of each of the ribs 205 (e.g., as indicated by the regression points 610). Therefore, the regression lines 615 are used to predict the curvature of the ribs 205. The regression lines 615 that are shown in FIG. 6B may be regressed together to ensure that they are parallel. From the regression lines 615, the transverse view line in the middle of the rib space (e.g., the mid-rib-space transverse plane 805) may be calculated (e.g., at step 510 of method 500) by identifying a midpoint between the two regression lines 615. In some embodiments, the processing circuit 114 (e.g., the AI circuit 122) may be configured to apply one of several algorithms retrieved from the external database 120 for calculating the regression lines 615. In some instances where the regression points 610 include outliers and/or missing intersection points, the algorithms used to calculate the regression lines 615 may be robust to such errors.

Although FIGS. 5, 6A, and 6B describe detecting a rib orientation using a plurality of sagittal views (e.g., the several sagittal views acquired at step 506, the plurality of sagittal planes 605, etc.), it should be appreciated that the rib orientation may similarly be detected using a plurality of elevation planes (e.g., several of the elevation planes 215). That is, step 506 of method 500 may include acquiring several elevation planes instead of or in addition to the several sagittal views. Each of the elevation planes may be defined by a distinct angle, and an elevation plane with the angle at which a longest pleura (e.g., pleural line 710) is seen may be selected in order to detect the rib orientation.

Referring to FIG. 7, an ultrasound image 700 acquired from a sagittal view using the ultrasound probe 106 is shown. As shown, the ultrasound image 700 depicts the ribs 205 and the regression lines 615 generated using the orientation 600 as shown in FIG. 6B. The ultrasound image 700 also depicts rib shadows 705 for each of the ribs 205, and a pleural line 710. The term pleural line, as used herein, refers to the pleura and/or pleural region depicted in the ultrasound image data. As shown, the rib shadows 705 may align with the regression lines 615, thus indicating that the regression lines 615 estimate the edge lines of the ribs 205. The pleural line 710 is shown as a line between the rib shadows 705 and represents the tissue surrounding the lung. Because the ultrasound image 700 is captured from a sagittal view (e.g., with an indicator of the probe 106 pointing towards the patient's head), the rib 205 and the rib shadow 705 on the lefthand side of the ultrasound image 700 represent an upper rib bone of the ribs 205 (e.g., a rib bone proximate to the patient's head). Similarly, the rib 205 and the rib shadow 705 on the righthand side of the ultrasound image 700 represent a lower rib bone of the ribs 205 (e.g., a rib bone proximate to the patient's feet).

Figure 8A:
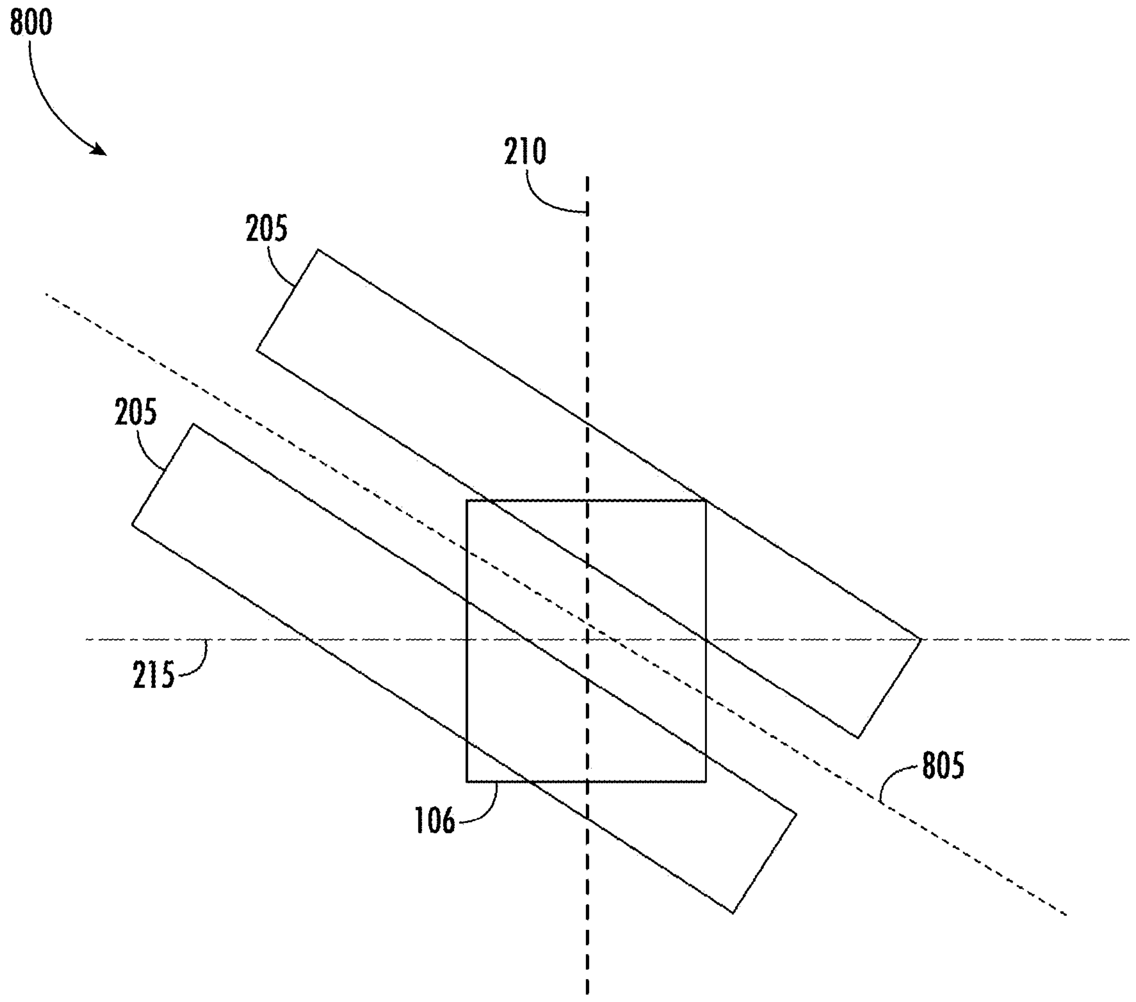
FIG. 8A is a first diagram of an orientation of the ultrasound probe used in the in the ultrasound imaging system of FIG. 1, according to an example embodiment.
Figure 8B:
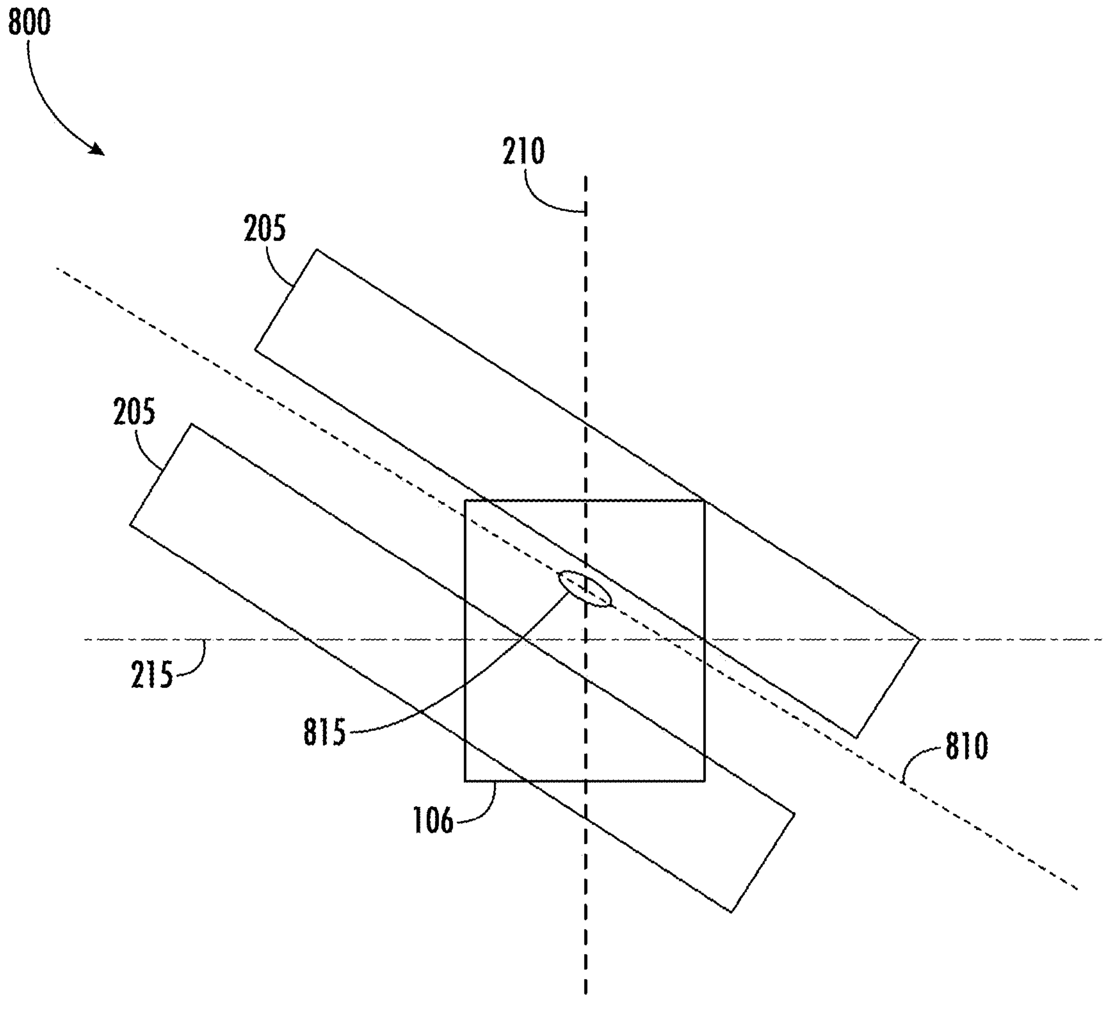
FIG. 8B is a second diagram of the orientation of the ultrasound probe used in the in the ultrasound imaging system of FIG. 1, according to an example embodiment.
Figure 8C:
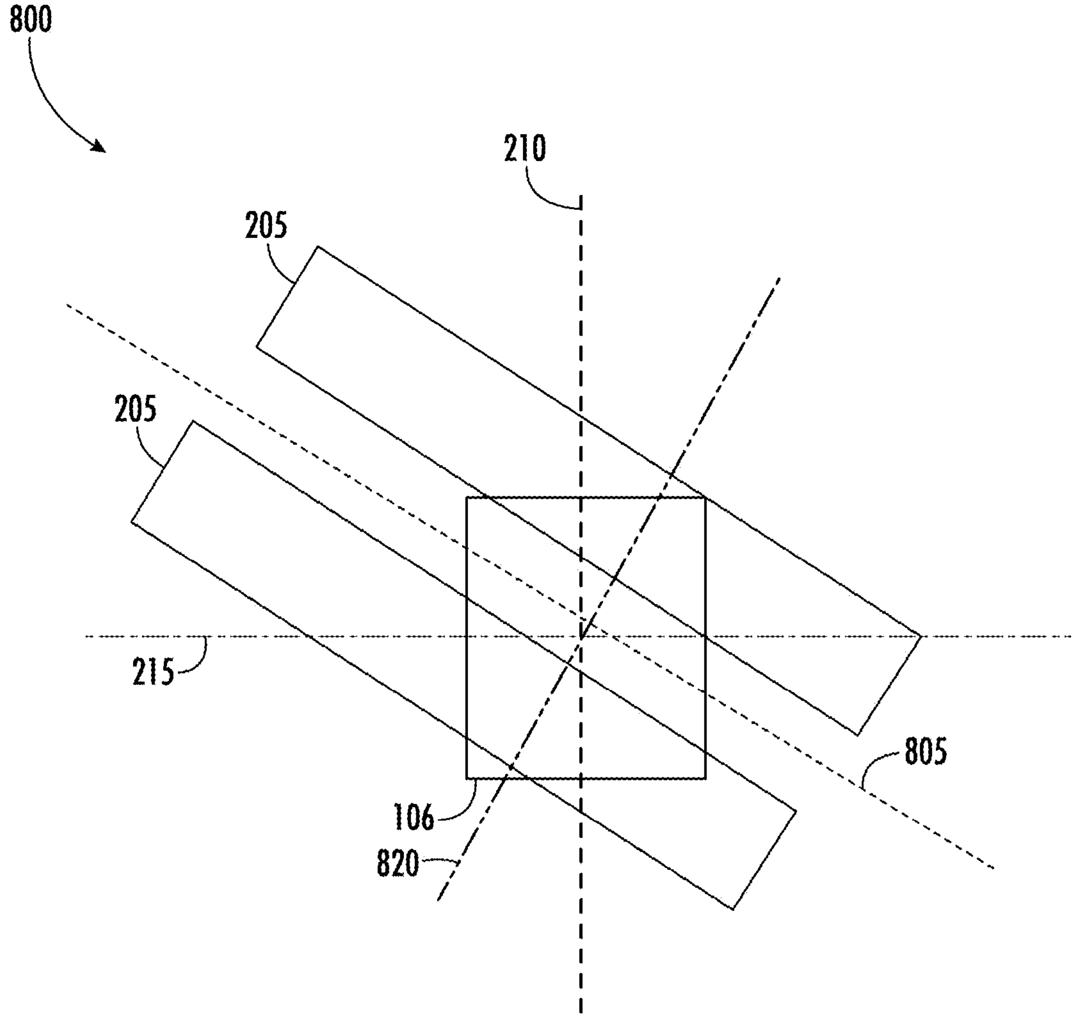
FIG. 8C is a third diagram of the orientation of the ultrasound probe used in the in the ultrasound imaging system of FIG. 1, according to an example embodiment.

Referring to FIGS. 8A-8C, variations of an orientation 800 of the ultrasound probe 106 relative to the ribs 205 are shown. According to each of the variations, the orientation 800 may be defined by the azimuthal plane 210, the elevation plane 215, and a transverse plane. For example, as shown in FIG. 8A, the transverse plane may include a mid-rib-space transverse plane 805. The mid-rib-space transverse plane 805 may represent the transverse plane determined at step 415 and/or the transverse view line calculated at step 510. That is, the mid-rib-space transverse plane 805 refers to a plane parallel with a direction of the ribs 205 and along a midpoint of the space between the ribs 205.

As shown in FIG. 8B, the transverse plane may include a pathology-centered transverse plane 810. For instance, where the image processing circuit 120 identifies a pathology (e.g., shown as pathology 815) from the image data obtained by the ultrasound probe 106, the orientation 800 may be automatically adjusted such that a transverse plane (e.g., the pathology-centered transverse plane 810) intersects the pathology 815. FIG. 8C shows the mid-rib-space transverse plane 805 and a cross-rib-space plane 820. As shown, the cross-rib-space plane 820 refers to a plane that is perpendicular to the mid-rib-space transverse plane 805, and therefore perpendicular to a direction of the ribs 205. In other words, FIG. 8C illustrates various embodiments in which, during a lung ultrasound scan, a sagittal plane (e.g., which may initially point in the direction of a patient's head) is also adjusted upon adjustment of the transverse plane (e.g., the mid-rib space transverse plane 805). Therefore, the adjusted sagittal plane may be perpendicular to the new transverse plane.

Figure 9A:
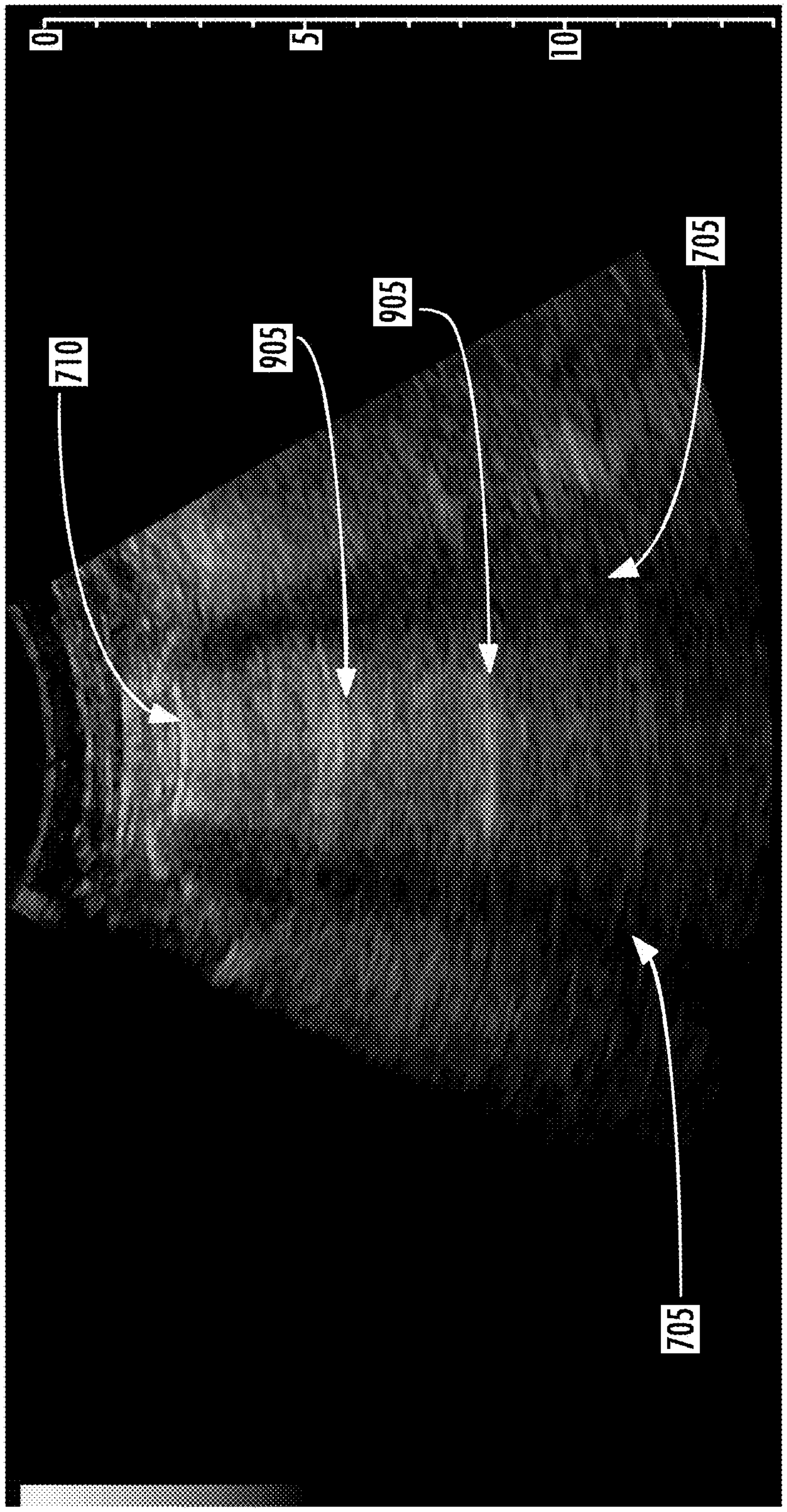
FIG. 9A is an illustration of a first ultrasound image acquired using a first type of ultrasound probe, according to an example embodiment.
Figure 9B:
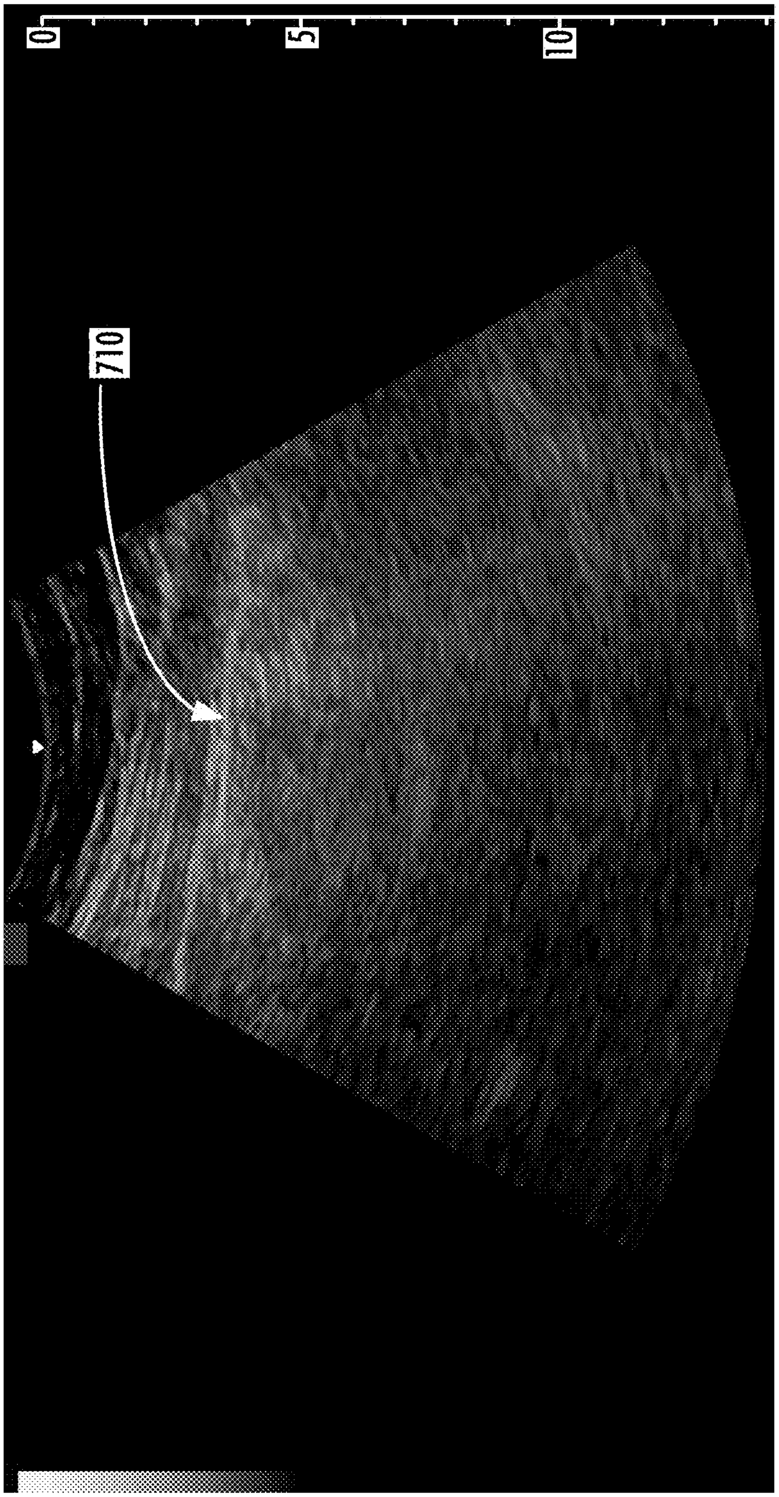
FIG. 9B is an illustration of a second ultrasound image acquired using the first type of ultrasound probe, according to an example embodiment.

Referring to FIGS. 9A and 9B, a first ultrasound image 900*a* and a second ultrasound image 900*b* acquired using a first type of ultrasound probe are shown. The first ultrasound image 900*a* is shown from a sagittal view, and therefore may refer to an image from the first image dataset received at step 405 of method 400. The second ultrasound image 900*b* is shown from a transverse view, and therefore may refer to the second image data received at step 425 of method 400. As shown in FIG. 9A, the first ultrasound image 900*a* depicts the rib shadows 705, the pleural line 710, and A-lines 905. The second ultrasound image 900*b* is shown to include the pleural line 710.

Because lungs cannot be directly imaged using an ultrasound probe (e.g., due to the lungs being full of air, as described herein), lung ultrasounds are artifact-based. In other words, rather than the ultrasound signals back-scattering from the anatomical feature itself (e.g., the lung), as in other ultrasounds such as an echocardiogram (e.g., where the ultrasound signals back-scatter from the heart/the various components thereof), the ultrasound images include represent the anatomical feature using A-line artifacts (e.g., the A-lines 905). The A-lines 905 are a reverberation artifact that occurs when the ultrasound signals reverberate between the transducer and the air within the lung. therefore, the A-lines 905 may be used to infer the location and depiction of the lung within ultrasound images, despite the probe 106 being unable to capture an image of the lung itself. In some embodiments, where there is a pathology within the ultrasound image, a B-line may replace the A-lines 905.

Figure 10:
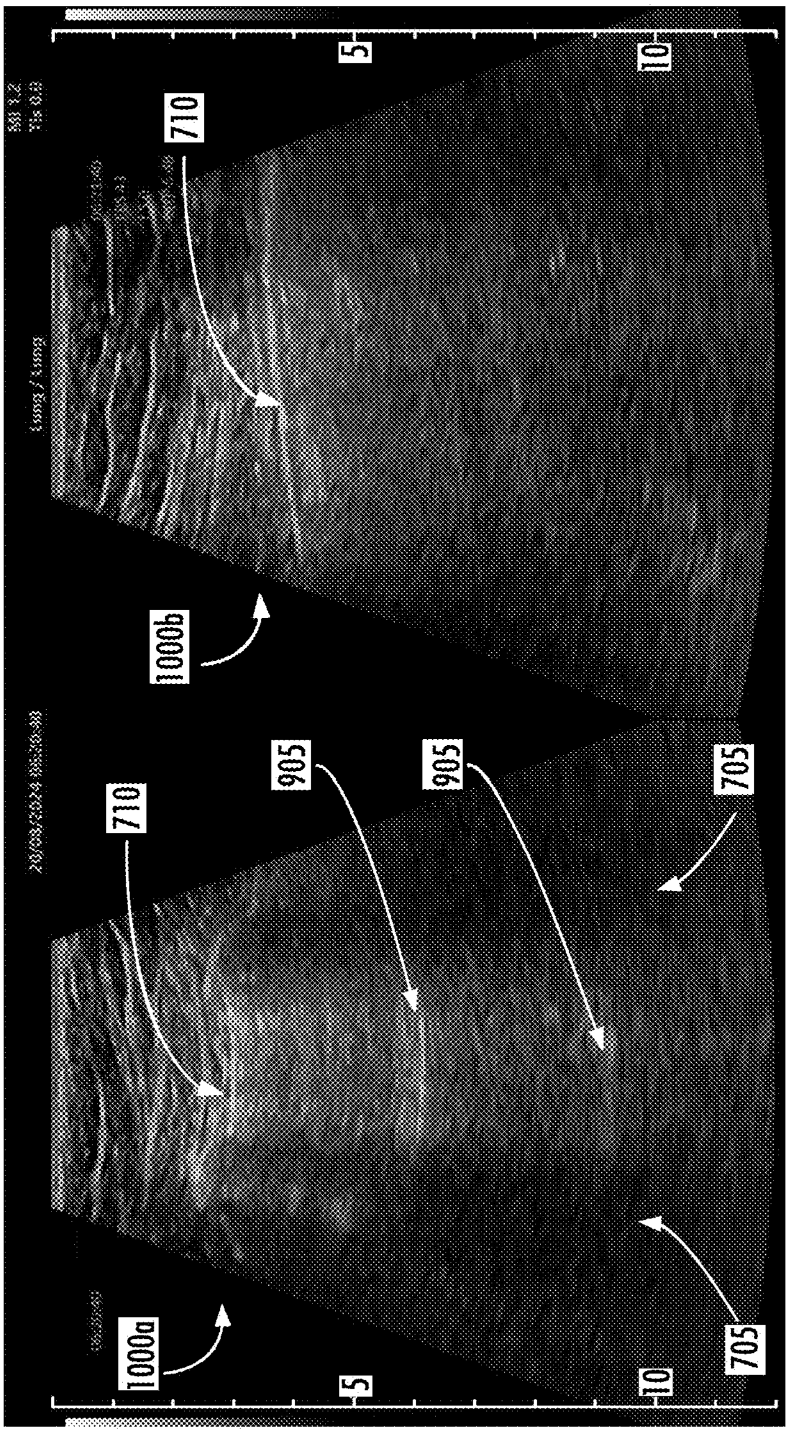
FIG. 10 is an illustration of a first ultrasound image and a second ultrasound image acquired using a second type of ultrasound probe, according to an example embodiment.

Referring to FIG. 10, a first ultrasound image 1000*a* and a second ultrasound image 1000*b* acquired using a second type of ultrasound probe are shown. The first ultrasound image 1000*a* is shown from a sagittal view, and therefore may refer to an image from the first image dataset received at step 405 of method 400. The second ultrasound image 1000*b* is shown from a transverse view, and therefore may refer to the second image data received at step 425 of method 400. As shown in FIG. 10, the first ultrasound image 1000*a* depicts the rib shadows 705, the pleural line 710, and the A-lines 905. The second ultrasound image 1000*b* is shown to include the pleural line 710.

The embodiments described herein have been described with reference to drawings. The drawings illustrate certain details of specific embodiments that provide the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As utilized herein, terms of degree such as "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that terms such as "exemplary," "example," and similar terms, as used herein to describe various embodiments, are intended to indicate that such embodiments are possible examples, representations, or illustrations of possible embodiments, and such terms are not intended to connote that such embodiments are necessarily extraordinary or superlative examples.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any element on its own or any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the drawings. It should be noted that the orientation of various elements may differ according to other exemplary embodiments, and that such variations are intended to be encompassed by the present disclosure.

As used herein, terms such as "engine" or "circuit" may include hardware and machine-readable media storing instructions thereon for configuring the hardware to execute the functions described herein. The engine or circuit may be embodied as one or more circuitry components including, but not limited to, processing circuitry, network interfaces, peripheral devices, input devices, output devices, sensors, etc. In some embodiments, the engine or circuit may take the form of one or more analog circuits, electronic circuits (e.g., integrated circuits (IC), discrete circuits, system on a chip (SOCs) circuits, etc.), telecommunication circuits, hybrid circuits, and any other type of circuit. In this regard, the engine or circuit may include any type of component for accomplishing or facilitating achievement of the operations described herein. For example, an engine or circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

An engine or circuit may be embodied as one or more processing circuits comprising one or more processors communicatively coupled to one or more memory or memory devices. In this regard, the one or more processors may execute instructions stored in the memory or may execute instructions otherwise accessible to the one or more processors. The one or more processors may be constructed in a manner sufficient to perform at least the operations described herein. In some embodiments, the one or more processors may be shared by multiple engines or circuits (e.g., engine A and engine B, or circuit A and circuit B, may comprise or otherwise share the same processor which, in some example embodiments, may execute instructions stored, or otherwise accessed, via different areas of memory).

Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be provided as one or more suitable processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given engine or circuit or components thereof may be disposed locally (e.g., as part of a local server, a local computing system, etc.) or remotely (e.g., as part of a remote server such as a cloud based server). To that end, engines or circuits as described herein may include components that are distributed across one or more locations.

An example system for providing the overall system or portions of the embodiments described herein might include one or more computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

Although the drawings may show and the description may describe a specific order and composition of method steps, the order of such steps may differ from what is depicted and described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions, and arrangement of the embodiments without departing from the scope of the present disclosure as expressed in the appended claims.

What is claimed is:

1. An ultrasound imaging system comprising:

a processing circuit having a processor coupled to a memory device storing instructions thereon that, when executed, cause the processing circuit to perform operations comprising:

receiving a first image dataset obtained by an ultrasound probe along two or more parallel planes of a first orientation, the first orientation in a field of view of the ultrasound probe;

identifying at least one secondary anatomical feature based on the first image dataset, the at least one secondary anatomical feature identified in each of the two or more parallel planes;

determining an additional plane oriented according to the identification of the at least one secondary anatomical feature in the two or more parallel planes;

automatically aligning a scanning plane of the ultrasound probe with the additional plane;

receiving second image data obtained by the ultrasound probe along the additional plane; and displaying a bi-plane image on a display device of the ultrasound imaging system, wherein the bi-plane image is based on an image from the first image dataset and the second image data.

2. The ultrasound imaging system of claim 1, wherein:

identifying the at least one secondary anatomical feature is based on intersections between the at least one secondary anatomical feature and each of the two or more parallel planes; and the additional plane is oriented according to points of the intersections.

3. The ultrasound imaging system of claim 1, wherein the ultrasound probe comprises a three-dimensional matrix probe.

4. The ultrasound imaging system of claim 1, wherein the operations further comprise:

detecting a pathology in the first image dataset; and determining the additional plane such that the additional plane intersects with a location of the pathology.

5. The ultrasound imaging system of claim 1, wherein the operations further comprise:

identifying, based on the first image dataset, at least two intersection points, each of the at least two intersection points defined by an intersection between each of the two or more parallel planes and the at least one secondary anatomical feature;

estimating a line based on the at least two intersection points, the estimated line defining the at least one secondary anatomical feature; and determining the additional plane oriented according to the estimated line in the field of view.

6. The ultrasound imaging system of claim 1, wherein the at least one secondary anatomical feature comprises two rib bones, and wherein the first orientation is a sagittal plane and the additional plane is a transverse plane parallel to the two rib bones.

7. The ultrasound imaging system of claim 6, wherein the operations further comprise, prior to determining the additional plane, assessing the two rib bones.

8. The ultrasound imaging system of claim 7, wherein the assessing the two rib bones comprises:

estimating, using the sagittal plane, a space between the two rib bones; and regressing one or more edge lines of the two rib bones.

9. The ultrasound imaging system of claim 8, wherein the operations further comprise calculating a midpoint of the space between the two rib bones, and wherein the transverse plane is along the midpoint of the space between the two rib bones.

10. The ultrasound imaging system of claim 1, wherein the first image dataset and the second image data depict a primary anatomical feature.

11. The ultrasound imaging system of claim 10, wherein the primary anatomical feature comprises a lung, and wherein the second image data is obtained by the ultrasound probe according to a frequency of a breathing cycle of a patient from whom the first image dataset and the second image data are obtained.

12. An ultrasound imaging system comprising:

an image processing circuit configured to identify at least one secondary anatomical feature based on a first image dataset obtained by an ultrasound probe along two or more parallel planes of a first orientation in a field of view of the ultrasound probe, the at least one secondary anatomical feature identified in each of the two or more parallel planes, and wherein an additional plane is oriented according to the identification of the at least one secondary anatomical feature in the two or more parallel planes, wherein second image data is obtained by the ultrasound probe along the additional plane;

a control circuit configured to automatically align a scanning plane of the ultrasound probe with the additional plane; and a display device configured to display a bi-plane image based on an image from the first image dataset and the second image data.

13. The ultrasound imaging system of claim 12, wherein the first image dataset and the second image data depict a primary anatomical feature, wherein the primary anatomical feature is a lung.

14. The ultrasound imaging system of claim 12, wherein the at least one secondary anatomical feature comprises two rib bones, and wherein the first orientation is a sagittal plane and the additional plane is a transverse plane parallel to the two rib bones.

15. The ultrasound imaging system of claim 14, wherein the image processing circuit is further configured to:

estimate, using the sagittal plane, a space between the two rib bones;

regress one or more edge lines of the two rib bones; and calculate a midpoint of the space between the two rib bones, wherein the transverse plane is along the midpoint of the space between the two rib bones.

16. A method comprising:

receiving, by a processing circuit of an ultrasound imaging system, a first image dataset obtained by an ultrasound probe along two or more parallel planes of a first orientation, the first orientation in a field of view of the ultrasound probe;

identifying, by the processing circuit, at least one secondary anatomical feature based on the first image dataset, the at least one secondary anatomical feature identified in each of the two or more parallel planes;

determining, by the processing circuit, an additional plane oriented according to the identification of the at least one secondary anatomical feature in the two or more parallel planes;

automatically aligning, by the processing circuit, a scanning plane of the ultrasound probe with the additional plane;

receiving, by the processing circuit, second image data obtained by the ultrasound probe along the additional plane; and displaying, by the processing circuit, a bi-plane image on a display device of the ultrasound imaging system.

17. The method of claim 16, wherein the at least one secondary anatomical feature comprises two rib bones, and wherein the first orientation is a sagittal plane and the additional plane is a transverse plane parallel to the two rib bones.

18. The method of claim 17, further comprising:

estimating, by the processing circuit using the sagittal plane, a space between the two rib bones;

regressing, by the processing circuit, one or more edge lines of the two rib bones; and calculating, by the processing circuit, a midpoint of the space between the two rib bones, wherein the transverse plane is along the midpoint of the space between the two rib bones.

19. The method of claim 16, wherein the first image dataset and the second image data depict a primary anatomical feature.

20. The method of claim 19, wherein the primary anatomical feature is a lung.

* * * * *